US010449321B2

(12) United States Patent
Meyerhoff et al.

(10) Patent No.: US 10,449,321 B2
(45) Date of Patent: Oct. 22, 2019

(54) GAS DELIVERY DEVICES

(71) Applicant: The Regents of the University of Michigan, Ann Arbor, MI (US)

(72) Inventors: Mark E. Meyerhoff, Ann Arbor, MI (US); Nicolai Lehnert, Ann Arbor, MI (US); Yu Qin, Ann Arbor, MI (US); Andrew P. Hunt, Ann Arbor, MI (US); Elizabeth J. Brisbois, Ann Arbor, MI (US); Hang Ren, Salt Lake City, UT (US)

(73) Assignee: The Regents of the University of Michigan, Ann Arbor, MI (US)

( * ) Notice: Subject to any disclaimer, the term of this patent is extended or adjusted under 35 U.S.C. 154(b) by 310 days.

(21) Appl. No.: 15/484,981

(22) Filed: Apr. 11, 2017

(65) Prior Publication Data
US 2017/0216550 A1 Aug. 3, 2017

Related U.S. Application Data

(60) Continuation-in-part of application No. 15/226,769, filed on Aug. 2, 2016, which is a division of
(Continued)

(51) Int. Cl.
*A61M 16/12* (2006.01)
*A61M 1/16* (2006.01)
(Continued)

(52) U.S. Cl.
CPC .............. *A61M 16/12* (2013.01); *A61K 33/00* (2013.01); *A61M 1/1698* (2013.01);
(Continued)

(58) Field of Classification Search
CPC .............. A61M 16/00; A61M 16/0003; A61M 16/0057; A61M 16/10; A61M 16/12;
(Continued)

(56) References Cited

U.S. PATENT DOCUMENTS 3,726,777 A 4/1973 Macur
4,834,101 A 5/1989 Collision et al.
(Continued)

FOREIGN PATENT DOCUMENTS

WO WO 95-07610 3/1995
WO WO-2018191364 A1 * 10/2018 .......... A61M 1/1698

OTHER PUBLICATIONS

Oh, Bong Kyun, et al. "Catalytic Generation of Nitric Oxide from Nitrite at the Interface of Polymeric Films Doped with Lipophilic Cu(II)-Complex: A Potential Route to the Preparation of Thromboresistent Coatings", Biomaterials, Jan. 2004, vol. 25, No. 2, pp. 283-293.
(Continued)

*Primary Examiner* — Joseph D. Boecker
(74) *Attorney, Agent, or Firm* — Dierker & Kavanaugh, P.C.

(57) ABSTRACT

A gas delivery device includes a nitric oxide generating system. The system has a medium including a source of nitrite ions. A working electrode is in contact with the medium. A Cu(II)-ligand complex is in contact with the working electrode. A reference/counter electrode is, or a reference electrode and a counter electrode are in contact with the medium and separated from the working electrode. An inlet conduit is to deliver nitrogen gas to the medium, and an outlet conduit is to transport a stream of nitrogen gas and nitric oxide from the medium. An inspiratory gas conduit is operatively connected to the outlet conduit to introduce an oxygen-containing gas and form an output gas stream of the gas delivery device.

29 Claims, 9 Drawing Sheets

Related U.S. Application Data application No. 14/099,942, filed on Dec. 7, 2013, now Pat. No. 9,480,785, which is a continuation-in-part of application No. 13/852,841, filed on Mar. 28, 2013, now Pat. No. 9,498,571.

(60) Provisional application No. 61/617,886, filed on Mar. 30, 2012.

(51) Int. Cl.

| A61M 1/34 | (2006.01) |
|---|---|
| A61M 16/08 | (2006.01) |
| A61M 16/10 | (2006.01) |
| A61M 25/00 | (2006.01) |
| A61M 35/00 | (2006.01) |
| A61K 33/00 | (2006.01) |

(52) U.S. Cl.
CPC .......... *A61M 1/342* (2013.01); *A61M 1/3462* (2013.01); *A61M 25/0043* (2013.01); *A61M 35/00* (2013.01); *A61M 16/0875* (2013.01); *A61M 2016/1025* (2013.01); *A61M 2016/1035* (2013.01); *A61M 2025/0057* (2013.01); *A61M 2202/0208* (2013.01); *A61M 2202/0275* (2013.01)

(58) Field of Classification Search
CPC ........ A61M 16/125; A61M 2016/1025; A61M 2016/1035; A61M 2202/0208; A61M 2202/0275; A61M 1/1698; A61M 1/342; A61M 1/3462

See application file for complete search history.

(56) References Cited

U.S. PATENT DOCUMENTS

| 5,396,882 | A | | 3/1995 | Zapol |
|---|---|---|---|---|
| 5,827,420 | A | * | 10/1998 | Shirazi .................. A61M 16/10 205/220 |
| 6,097,976 | A | | 8/2000 | Yang et al. |
| 7,025,869 | B2 | | 4/2006 | Fine et al. |
| 7,040,313 | B2 | | 5/2006 | Fine et al. |
| 7,407,570 | B2 | | 8/2008 | Prince et al. |
| 8,101,589 | B2 | | 1/2012 | Arnold et al. |
| 8,741,222 | B2 | | 6/2014 | Fine et al. |
| 2003/0062043 | A1 | | 4/2003 | Fine et al. |
| 2003/0064028 | A1 | | 4/2003 | Fine et al. |
| 2004/0224868 | A1 | | 11/2004 | Meyerhoff et al. |
| 2006/0008529 | A1 | | 1/2006 | Meyerhoff et al. |
| 2007/0270674 | A1 | | 11/2007 | Kane et al. |
| 2008/0226686 | A1 | | 9/2008 | Meyerhoff et al. |
| 2008/0262330 | A1 | | 10/2008 | Reynolds et al. |
| 2010/0051480 | A1 | | 3/2010 | Schoenfisch et al. |
| 2013/0261537 | A1 | * | 10/2013 | Hofler ............... A61M 25/0043 604/23 |
| 2014/0294672 | A1 | * | 10/2014 | Meyerhoff ............ A61M 1/342 422/48 |
| 2016/0228670 | A1 | | 8/2016 | Av-Gay et al. |
| 2016/0339197 | A1 | | 11/2016 | Meyerhoff et al. |

OTHER PUBLICATIONS

Chi, et al. Electrochemical Generation of Free Nitric Oxide from Nitrite Catalyzed by Iron meso-Tetrakis (4-N-methylpyridiniumyl), Porphyrin, Inorg.Chem. 2004, 43, pp. 8437-8446.

Komeda, et al. "Mol Struct of Nitro- and Nitrito-Copper Comp as Reaction Intermed in Electrochem Reduction of Nitrite to Dinitrogen Oxide", Bull.Chem.Soc.Jpn, 68, pp. 581-589 (1995).

International Search Report and Written Opinion for PCT/US2013/034425 dated Jul. 18, 2013, 17 pages.

Zheng, et al. "Highly Sensitive Amperometric Pt-Nafion Gas Phase Nitric Oxide Sensor: Performance and Application in Characterizing Nitric Oxide-Releasing Biomaterials", Analytica Chimica Acta 887, 2015, pp. 186-191.

Hofler, Lajos, et al. "Electromodulated Release of Nitric Oxide through Polymer Material from Reservoir of Inorganic Nitrite Salt", RSC Advances, Jul. 12, 2012, 3 pages.

James, et al. "Nitric Oxide Administration During Paediatric Cardiopulmonary Bypass: A Randomised Controlled Trial", Intensive Care Med (2014) 42:1744-1752.

* cited by examiner

GAS DELIVERY DEVICES

CROSS-REFERENCE TO RELATED APPLICATIONS

This application is a continuation-in-part application of co-pending U.S. Ser. No. 15/226,769, filed Aug. 2, 2016, which itself is a divisional application of U.S. Ser. No. 14/099,942, filed Dec. 7, 2013 (now U.S. Pat. No. 9,480,785), which itself is a continuation-in-part application of U.S. Ser. No. 13/852,841, filed Mar. 28, 2013 (now U.S. Pat. No. 9,498,571), which itself claims the benefit of U.S. Provisional Application Ser. No. 61/617,886, filed Mar. 30, 2012, each of which is incorporated by reference herein in its entirety.

STATEMENT REGARDING FEDERALLY SPONSORED RESEARCH OR DEVELOPMENT

This invention was made with government support under Grant Nos. HD087071 and HL119403 awarded by the National Institutes of Health (NIH). The government has certain rights in the invention.

BACKGROUND

Nitric oxide (NO) is an endogenous gas molecule that has been shown to have several important physiological functions, including its unique vasodilating properties, wound healing properties, angiogenesis promoting properties, cancer-fighting potency, anti-platelet activity, and anti-microbial/anti-viral activity. In some instances, NO can be used to control infection, prevent biofilm formation, and minimize inflammation and fibrosis.

The use of NO in inhalation therapy has also been explored. Inhaled nitric oxide has been used to treat lung failure, and has been shown to enhance pulmonary vasodilation and lower pulmonary vascular resistance. Inhaled nitric oxide has also been used to treat neonates with hypoxic respiratory failure, and has been shown to improve oxygenation and to reduce the need for extracorporeal membrane oxygenation therapy. The use of inhaled nitric oxide may prove to be beneficial in other areas as well, such as during lung transplants, for treating pulmonary hypertension, as an inhaled antiseptic agent, etc.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1A:
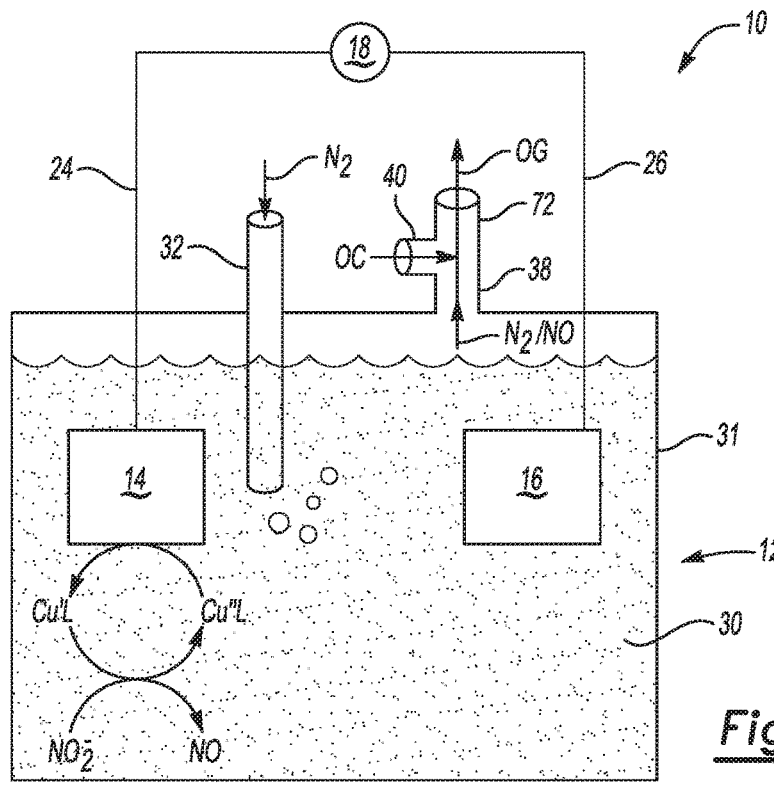
FIG. 1A is a schematic view of an example of a gas delivery device including a two-electrode configuration.

Several examples of gas delivery devices are disclosed herein. In the example devices, nitric oxide (NO) gas is generated electrochemically on demand from a solution reservoir containing a copper(II) ligand complex (i.e., Cu(II)-ligand complex) and a dissolved source of nitrite. The devices disclosed herein eliminate the need for nitric oxide tanks (i.e., NO in compressed gas cylinders), which simplifies the device and reduces the cost of the device.

Moreover, with the example gas delivery devices disclosed herein, the amount of NO that is generated may be precisely controlled by varying the voltage or current applied to a working electrode. This enables a suitable amount of NO to be generated in order to obtain a desired effect in a particular application. As one example, a steady therapeutic dose (e.g., from about 100 ppbv (parts per billion by volume) to about 100 ppmv (parts per million by volume)) of NO may be generated for inhaled nitric oxide treatments. The concentration of the NO in the output gas stream also depends, at least in part, on the flow rate of the gas(es) utilized. As another example, periodic or continuous NO generation may be used in the sweep gas of a blood oxygenator to deliver the NO to blood in order to reduce platelet activation and consumption during extracorporeal life support or cardiopulmonary bypass.

More specifically, the example gas delivery devices disclosed herein utilize a Cu(II)-ligand complex, which is in contact with the working electrode. It is to be understood that any "contact" between the Cu(II)-ligand complex and the working electrode that enables the Cu(II)-ligand complex to function as an electron mediator may be utilized. As one example, the Cu(II)-ligand complex may be in contact with the working electrode when it is dissolved or dispersed in the medium in which the working electrode is placed. As another example, the Cu(II)-ligand complex may be in contact with the working electrode by being immobilized on a surface of the working electrode. By "immobilized," it is meant that the Cu(II)-ligand complex can be covalently attached to the working electrode, physically adsorbed to the working electrode, or doped in or covalently attached to a polymer, thin film, or hydrogel that is deposited on the working electrode surface.

These Cu(II)-ligand complexes enable one to perform an electrochemical method that uses a cathodic voltage or a cathodic current alone to generate and modulate the release of NO. In these examples, the NO is electrochemically generated by reducing the Cu(II)-ligand complex to a Cu(I)-ligand complex, the Cu(I) of which then functions to reduce nitrite ions ($NO_2^-$) to NO. The NO that is generated is not bound to the reduced Cu(I) center of the ligand complex, and thus is capable of being transported out of the medium in which is it generated without performing additional steps to oxidize the ligand complex. The ratio of Cu(I)-ligand complex to Cu(II)-ligand complex at or near the surface of an inert working electrode can be controlled by controlling the applied potential or current. This enables one to control the amount of NO generated for a given concentration of nitrite and Cu(II)-ligand complex.

Any of the examples of the gas delivery device disclosed herein include a nitric oxide (NO) generating system. The NO generating system includes a medium including a source of nitrite ions; a working electrode in contact with the medium; a Cu(II)-ligand complex in contact with the working electrode; and one of: a reference/counter electrode or a reference electrode and a counter electrode in contact with the medium and separated from the working electrode. The gas delivery device further includes an inlet conduit to deliver nitrogen gas to the medium, an outlet conduit to transport a stream of nitrogen gas and nitric oxide from the medium, and an inspiratory gas conduit operatively connected to the outlet conduit to introduce an oxygen-containing gas and form an output gas stream of the gas delivery device.

Figure 1B:
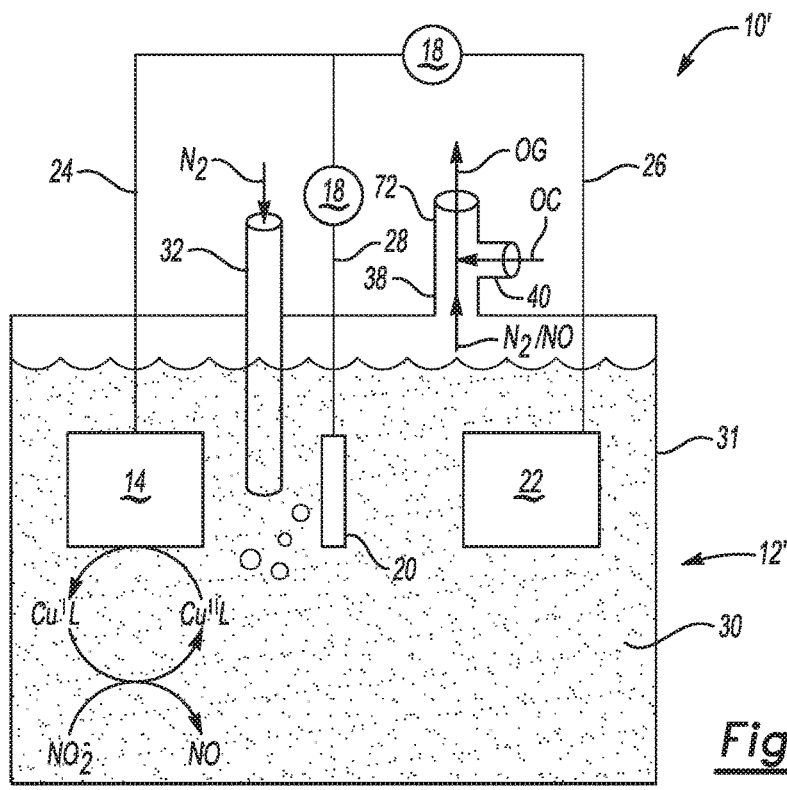
FIG. 1B is a schematic view of an example of the gas delivery device including a three-electrode configuration.

Two examples of the gas delivery device 10, 10' and the associated NO generating system 12, 12' are respectively shown in FIGS. 1A and 1B. The NO generating system 12 in FIG. 1A is a two-electrode system, and the NO generating system 12' in FIG. 1B is a three-electrode system.

In the two-electrode configuration of FIG. 1A, a working electrode 14 and a reference or counter electrode (referred to herein as a reference/counter electrode 16) are used. In the two-electrode system, the reference and counter electrodes are shorted on the same electrode 16. In this system, current passes through the reference/counter electrode 16, and the potential across the complete cell can be measured. The working electrode 14 and reference/counter electrode 16 are electrically connected to a potentiostat/galvanostat 18.

In the three-electrode configuration of FIG. 1B, the working electrode 14 is used in conjunction with a separate reference electrode 20 and a separate counter electrode 22. In this system, current flows between the counter electrode 22 and the working electrode 14, and the potential difference is controlled between these electrodes 22, 14. The potential difference is measured between the working electrode 14 and the reference electrode 20.

In both the two-electrode and the three-electrode systems, the potentiostat/galvanostat 18 may be used to operate the circuit. The potentiostat/galvanostat 18 may include a control amplifier to force current to flow through the cell. The reference/counter electrode 16 or the counter electrode 22 may be connected to the output of the control amplifier. The potentiostat/galvanostat 18 may also include components for measuring current (e.g., a current follower for low current and/or a shunt for high current) and for measuring the potential difference (e.g., a differential amplifier).

In some of the examples disclosed herein, the potentiostat/galvanostat 18 may be switched between potentiostatic mode and galvanostatic mode.

In potentiostatic mode, the potentiostat/galvanostat 18 will accurately control the potential of the working electrode 14 so that the potential difference between the working electrode 14 and the reference electrode 20 or reference/counter electrode 16 is well defined, and corresponds to a specified value. In the examples disclosed herein, the potentiostatic mode may be used to apply a desired cathodic voltage. The application of a constant voltage can be used to produce a relatively constant level of NO.

In galvanostatic mode, the current flow between the working electrode 14 and the counter electrode 22 or the reference/counter electrode 16 is controlled. To maintain constant current, the voltage may be continuously adjusted, or adjusted as necessary. The potential difference between the working electrode 14 and the reference electrode 20 or reference/counter electrode 16 and the current flowing between the working electrode 14 and the counter electrode 22 or the reference/counter electrode 16 are continuously monitored in order to keep the current constant. For example, the cathodic voltage may be applied, and during the application of the cathodic voltage, the current at the working electrode may be monitored, and the cathodic voltage may be selectively adjusted to maintain an at least substantially constant current at the working electrode. As used herein, the "at least substantially constant current" is a current that is within ±5% of a set value. In one example, the current fluctuation is less than 0.005 mA. The application of the at least substantially constant current can be used to produce the NO, and this method may result in a more constant NO level than the voltage application method. In the examples disclosed herein, the galvanostatic mode is used to apply the desired and constant cathodic current.

It is to be understood that while a potentiostat/galvanostat 18 is described, any other potential source or current source may be used for performing the examples of the method disclosed herein.

The electrical connections between the various electrodes 14, 16, 20, 22 and the potentiostat/galvanostat 18 (or various components thereof) may be through conductive leads. For example, as shown in FIG. 1A, conductive leads 24 and 26 respectively and electrically connect the working electrode 14 and the reference/counter electrode 16. More specifically, the conductive leads 24, 26 electrically connect the respective electrodes 14, 16 to the potentiostat/galvanostat 18 that is used to control and monitor the applied voltage or current. For another example, as shown in FIG. 1B, conductive leads 24 and 26 respectively and electrically connect the working electrode 14 and the reference/counter electrode 16, and conductive lead 28 electrically connects the reference electrode 20 to the working and counter electrodes 14, 22. As illustrated, the conductive leads 24, 26, 28 electrically connect the respective electrodes 14, 22, 20 to the potentiostat/galvanostat 18 that is used to control and monitor the applied voltage or current. The conductive leads 24, 26, 28 may be made of any conductive material, examples of which include copper wires, platinum wires, stainless steel wires, aluminum wires, etc.

Any suitable working electrode 14 may be used. Examples of the working electrode 14 include platinum, gold, carbon (e.g., glassy carbon, carbon paste, carbon cloth, etc.) or a carbon coated material, mercury, stainless steel, a base electron conducting material having a thin film of platinum thereon, a base electron conducting material having a thin film of gold thereon, etc. Examples of the base electron material include platinum, gold, carbon or a carbon coated material, mercury, stainless steel, titanium, a metal coated polymer, a conductive polymer, a semiconductor (e.g., silicon, etc.), or the like. In an example, the thin film of platinum or gold may have a thickness ranging from about 2 nm to about 10 μm. In another example, the thin film of platinum or gold may have a thickness ranging from about 10 nm to about 1 μm. The thin may be deposited on the base electrode using any suitable vapor deposition method. As example, platinum or gold may be deposited via chemical vapor deposition (CVD) or plasma enhanced chemical vapor deposition (PECVD) on a plastic mesh base electrode.

The working electrode 14 may have a relatively large surface area since (as shown schematically in both FIGS. 1A and 1B) the reaction of the Cu(II)-ligand complex used to electrochemically generate the NO takes place at the working electrode 14. The larger the surface area of the working electrode 14, the more NO that will be generated at a given current density or applied voltage. As such, the surface area of the working electrode 14 can depend, at least in part, on the desired concentration of NO and the flow rate that is to be used. In an example, the surface area of the working electrode 14 ranges from about 0.1 cm$^2$ to about 200 cm$^2$. In another example, the surface area of the working electrode 14 ranges from about 4 cm$^2$ to about 50 cm$^2$. In still another example, the surface area of the working electrode 14 ranges from about 15 cm$^2$ to about 25 cm$^2$.

In the two-electrode system, any suitable reference/counter electrode 16 may be used. For example, the reference/counter electrode 16 may be silver/silver chloride or some other reference electrode (e.g., mercury sulfate electrode, saturated calomel electrode) or pseudo reference electrode (e.g., gold, platinum, stainless steel, a sodium-selective electrode, a potassium-selective electrode, or the like). In an example of the three-electrode system, the reference electrode 22 is silver/silver chloride and the counter electrode 22 is platinum (e.g., a platinum mesh), gold, stainless steel, carbon (e.g., glassy carbon) or a carbon coated material, titanium, indium tin oxide (ITO), etc. In the three-electrode system, the reference electrode 22 may also be any of the previously mentioned reference electrodes or pseudo reference electrodes.

In an example, the electrodes 14, 16, 20, 22 may be in the form of mesh electrodes, which may be a network of wires or screen printed lines.

In both the two- and three-electrode systems, the medium 30 used to generate the NO includes a source of nitrite ions. In some examples, the medium 30 also has the Cu(II)-ligand complex dissolved or dispersed therein.

In an example, the source of nitrite ions in the medium 30 may be a water soluble, inorganic nitrite salt in an aqueous solution (e.g., water) or a hydrogel (e.g., hydroxymethylcellulose, poly(vinyl alcohol) (PVA), gelatin, etc.). Some examples of water soluble, inorganic nitrite salts include alkali metal nitrite salts and alkaline earth metal nitrite salts. Specific examples include nitrite salts of Li, Na, K, Rb, Ca, and Mg. Most other metal salts are also soluble in water, for example, Al salts and Fe salts. One specific example of the source of nitrite is sodium nitrite ($NaNO_2$). It is to be understood that ammonium nitrite or organic ammonium nitrite salts (e.g., $R_4N^+NO_2^-$ or $RNH_3^+NO_2^-$) could also be used, provided they are soluble in the aqueous phase. Tetramethylammonium nitrite and tetraethylammonium nitrite are specific examples of suitable water soluble, organic ammonium nitrite salts.

Using a high concentration of the nitrite salts in the medium 30 may significantly reduce the amount of $N_2O$ that may be generated during the electrochemical methods disclosed herein. In the examples disclosed herein, at least 100 mM nitrite is used as the medium 30, and amounts lower than 100 mM are generally not used, in part because higher levels of nitrite result in lower levels of $N_2O$. These levels of nitrite suppress the formation of $N_2O$ to negligible levels. As an example, a medium 30 including 400 mM nitrite may result in less than 5% $N_2O$ in the total gas species that is generated using the methods disclosed herein. It is believed that the excess nitrite competitively binds to the Cu center of the ligand complex (after the mediated reduction of nitrite to NO by the complex) so that the electrogenerated NO leaves the copper-ligand complex, rather than such a complex being reduced electrochemically again in the presence of another nitrite ion to form $N_2O$. This prevents the formation of significant levels of $N_2O$.

In addition, in some examples, the medium 30 includes the Cu(II)-ligand complex, which may also be water soluble. Examples of the Cu(II)-ligand complex are selected from the group consisting of Cu(II)-tri(2-pyridylmethyl)amine (CuTPMA), Cu(II)-tri(2-dimethylamino)ethyl]amine (CuMe$_6$Tren), Cu(II)-tri(2-pyridylmethyl)phosphine (CuTPMP), Cu(II)-1,4,7-trimethyl-1,4-7-triazacyclononane (Cu(Me₃TACN)), Cu(II)-1,4,7-triethyl-1,4-7-triazacyclononane (Cu(Et₃TACN)), Cu(II)-1,4,7-tripropyl-1,4-7-triazacyclononane (Cu(Pr₃TACN)), Cu(II)-1,4,7-triisopropyl-1,4-7-triazacyclononane (Cu(iPr₃TACN)), Cu(II)-(N,N-bis-(2-pyridylmethyl)amine-N-ethylate) (Cu(BMPA-Et)), Cu(II)-(N,N-bis-(2-pyridylmethyl)amine-N-propanoate) (Cu(BMPA-Pr)), Cu(II)-(N,N-bis-(2-pyridylmethyl)amine-N-butylate) (Cu(BMPA-Bu)), Cu(II)-(N,N-bis-(2-pyridylethyl)amine-N-ethylate) (Cu(BEPA-Et)), Cu(II)-(N,N-bis-(2-pyridylethyl)amine-N-propanoate) (Cu(BEPA-Pr)), Cu(II)-(N,N-bis-(2-pyridylethyl)amine-N-butylate (Cu(BEPA-Bu)), Cu(II)-(N,N-bis-(2-pyridylmethyl)amine-N-methyl-phenolate) (Cu(BMPA-MePhO)), Cu(II)-(N,N-bis-(2-pyridylmethyl)amine-N-ethyl-phenolate) (Cu(BMPA-EtPhO)), Cu(II)-(N,N-bis-(2-pyridylmethyl)amine-N-propyl-phenolate) (Cu(BMPA-PrPhO)), Cu(II)-(N,N-bis-(2-pyridylethyl)amine-N-methyl-phenolate) (Cu(BEPA-MePhO)), Cu(II)-(N,N-bis-(2-pyridylethyl)amine-N-ethyl-phenolate) (Cu(BEPA-EtPhO)), Cu(II)-(N,N-bis-(2-pyridylethyl)amine-N-propyl-phenolate) (Cu(BEPA-PrPhO)), Cu(II)-3-((2-(pyridin-2-yl)ethyl)(pyridin-2-ylmethyl)amino)ethylate (Cu(PEMA-Et)), Cu(II)-3-((2-(pyridin-2-yl)ethyl)(pyridin-2-ylmethyl)amino)propanoate (Cu(PEMA-Pr)), Cu(II)-3-((2-(pyridin-2-yl)ethyl)(pyridin-2-ylmethyl)amino)butylate (Cu(PEMA-Bu)), Cu(II)-2-(pyridin-2-yl)-N,N-bis(pyridin-2-ylmethyl)ethan-1-amine (Cu(PMEA)), Cu(II)-2,2'-(2-(2-(pyridin-2-yl)ethyl)butane-1,4-diyl)dipyridine (Cu(PMAP)), and combinations thereof. In an specific example, the Cu(II)-ligand complex may be selected from Cu(II)-tri(2-pyridylmethyl)amine (CuTPMA), Cu(II)-tri(2-dimethylamino)ethyl]amine (CuMe₆Tren), Cu(II)-tri(2-pyridylmethyl)phosphine (CuTPMP), and combinations thereof. These structures are shown below:

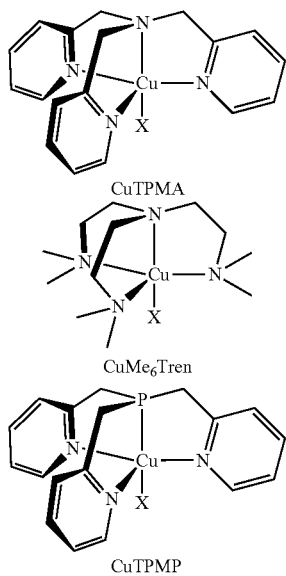

CuTPMA

CuMe₆Tren

CuTPMP

X = NO₂⁻ or H₂O

While several examples of the Cu(II)-ligand complex are provided herein, it is to be understood that other water soluble Cu(II)-complexes may be used. For example, Cu(II)-complexes that are not water soluble or have poor water solubility (i.e., <1 mM) may be used. An example of a Cu(II)-complex having poor water solubility is CuH₃thpa:

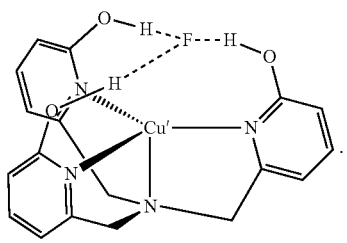

Any of the Cu(II)-complexes disclosed herein may be immobilized on the surface of the working electrode 14, rather than being dissolved or dispersed in the medium 30 from the outset of the method. As previously mentioned, the Cu(II)-complexes may be covalently attached to the working electrode 14, physically adsorbed to the working electrode14, or doped in or covalently attached to a polymer, thin film, or hydrogel that is deposited on the working electrode 14.

Examples of polymers that may be deposited on the working electrode 14 and that may have the Cu(II)-complex doped therein or covalently attached thereto include polyethylenimine, polyvinylimidazole, polypyrrole, polyurethane, or ion exchange membranes (e.g., NAFION®, from Dupont). The thin film that may be deposited on the working electrode 14 and that may have the Cu(II)-complex doped therein or covalently attached thereto may be any of those previously described (e.g., gold, platinum, etc.), or a self-assembled monolayer (SAM). Examples of suitable hydrogels that may be deposited on the working electrode 14 and that may have the Cu(II)-complex doped therein or covalently attached thereto may be any of those previously described (e.g., hydroxymethylcellulose, poly(vinyl alcohol) (PVA), gelatin, etc.).

In an example of the medium 30, the source of nitrite ions is any water soluble, inorganic or organic nitrite salt, and the Cu(II)-ligand complex is any of the examples set forth herein.

The medium 30 may also include a buffer and/or another additive that aids in driving the reduction reaction of Cu(I) with nitrite. Examples of suitable buffers are phosphate buffered saline (PBS), or 3-(N-morpholino)propanesulfonic acid (MOPS), or 4-(2-Hydroxyethyl)piperazine-1-ethanesulfonic acid (i.e., N-(2-Hydroxyethyl)piperazine-N'-(2-ethanesulfonic acid) (HEPES)). An example of another suitable additive is ethylenediaminetetraacetic acid (EDTA). EDTA helps drive the reduction reaction of Cu(I) with nitrite (Cu(I)+NO₂⁻+2H⁺Cu(II)+NO+H₂O) to the product side by chelating with Cu(II) stronger than with Cu(I).

Moreover, when a Ag/AgCl reference electrode 16, 20 is utilized, a fixed level of chloride ions is provided (e.g., as NaCl) in the medium 30 so that the reference electrode 16, 20 can maintain a constant potential (EMF).

When included in the medium 30, the Cu(II)-ligand complex may be present in a concentration ranging from about 0.1 mM to about 1 M, and the nitrite may be present in a concentration ranging from about 1 mM to the solubility limit of the nitrite (e.g., about 12 M for NaNO₂ at room temperature). In an example, a 1 M NaNO₂ solution may include from about 7 mM of the Cu(II)-ligand complex to about 14 mM of the Cu(II)-ligand complex. When immobilized on the surface of the working electrode 14, the Cu(II)-ligand complex may be a single monolayer or several layers that extend across the surface of the working electrode 14.

Each example NO generating system 12, 12' may include a reservoir or housing 31, that contains the medium 30 and the various electrodes 14, 16 or 14, 20, 22. The housing 31 may be made of any suitable material that can contain the medium 30 and the various electrodes 14, 16 or 14, 20, 22, and that is not permeable to nitrogen gas $N_2$ or to nitric oxide NO. Examples of suitable housing 31 materials include NO impermeable polymers (e.g., polytetrafluoroethylene (PTFE)), glass, etc. The housing 31 may be sealed around an inlet conduit 32 (used to introduce the nitrogen gas $N_2$) and an outlet conduit 38 (used to transport a stream of nitrogen gas and nitric oxide $N_2$/NO). The housing 31 may also be disposable so that the entire gas delivery device 10, 10' can be discarded at the end of its useful life, or it can include an opening through which the medium 30 and/or any of the electrodes 14, 16 or 14, 20, 22 can be replaced.

Examples of the method disclosed involve the electrochemical generation of nitric oxide using the nitric oxide generating system 12, 12', and the delivery of the nitric oxide using the gas delivery device 10, 10'. Some examples of the method involve applying a cathodic voltage or a cathodic current to the working electrode 14 positioned in contact with the medium 30 including the source of nitrite ions and the Cu(II)-ligand complex, thereby reducing the Cu(II)-ligand complex to a Cu(I)-ligand complex which reacts with nitrite from the source of nitrite ions to generate nitric oxide (NO); sweeping the nitric oxide using nitrogen gas to form a stream of nitrogen gas and nitric oxide; and introducing an oxygen-containing gas to mix with the stream of nitrogen gas and nitric oxide to form an output gas stream. Each of these steps is schematically shown in FIGS. 1A and 1B.

Electrochemical generation of nitric oxide using the two-electrode system of FIG. 1A or the three-electrode system of FIG. 1B involves immersing the electrodes 14, 16 or 14, 20, 22 in the medium 30, and applying the cathodic voltage to the working electrode 14 (e.g., using the previously described potentiostatic mode), or applying the cathodic current to the working electrode 14 (e.g., using the previously described galvanostatic mode). The cathodic voltage or current may be applied continuously, in pulses (e.g., more negative voltage followed by less negative voltage), or using a desirable on/off sequence. When applied, the cathodic voltage or cathodic current causes the Cu(II)-ligand complex $Cu^{II}L$ (in the medium 30 and/or on the working electrode 14) to electrochemically reduce on or near the working electrode 14 surface, which produces a high concentration of the Cu(I)-ligand complex $Cu^IL$ at or near the working electrode 14 surface (as shown in FIG. 1A, $Cu^{II} \rightarrow Cu^IL$). In turn, the Cu(I)-ligand complex $Cu^IL$ reacts directly with the nitrite ($NO_2^-$) in the medium 30 to generate nitric oxide gas (NO). In other words, the NO gas is generated by a one electron electrochemical reduction of $NO_2^-$ at the working electrode 14 using the Cu(II)-ligand complex $Cu^{II}L$ as an electron transfer mediator. The NO gas levels are produced at a rate dependent upon the applied cathodic voltage or the applied current (as will be described further hereinbelow).

The NO generated in the medium 30 is swept or purged from the medium 30 via a nitrogen gas $N_2$ that is introduced into the medium 30 via an inlet conduit 32 of the device 10, 10'. The nitrogen gas $N_2$ (also referred to herein as the nitrogen purge gas) may be supplied to the inlet conduit 32 from a gas source, such as a compressed gas tank 34 or an oxygen scrubber 36 (both of which are shown and further described in reference to FIG. 2). As such, it is to be understood that the nitrogen gas $N_2$ used to purge the NO from the medium 30 may be at least substantially pure nitrogen gas $N_2$ (e.g., delivered from the tank 34) or may be a mixed gas, which may be derived from ambient air that contains nitrogen gas, argon gas, carbon dioxide, and potentially small amounts of other non-oxygen gases, or may be a mixture of nitrogen gas and other inert gas(es). The nitrogen purge gas $N_2$ does not passivate the working electrode 14, and thus a cleaning process does not need to be performed throughout the electrochemical generation of NO. Moreover, unlike oxygen purge gas, the nitrogen purge gas $N_2$ does not react with the Cu(I)-ligand complex $Cu^IL$, and thus does not reduce the amount of Cu(I)-ligand complex $Cu^IL$ that is generated, and thus, in turn, also does not reduce the amount of NO that is generated. Additionally, the nitrogen purge gas $N_2$ does not react with the NO generated on the surface of the working electrode 14, which can lead to high NO generating efficiency. As such, the use of the nitrogen purge gas $N_2$ improves the stability (in terms of NO generation) and the performance of the devices 10, 10', when compared to similar devices that utilize an oxygen purge gas to remove the generated NO from solution.

In the example gas delivery devices 10, 10', the inlet conduit 32 delivers the nitrogen gas $N_2$ to the medium 30 in contact with the electrodes 14, 16 or 14, 20, 22. The inlet conduit 32 may be any suitable polymeric or other tubing attached to the gas source (not shown). The inlet conduit 32 is configured so that the nitrogen gas $N_2$ is introduced directly into the medium 30, and not into any headspace that may be present above the medium 30. The introduction of the nitrogen gas $N_2$ directly into the medium 30 causes bubbles to form in the medium 30 (as shown in FIGS. 1A and 1B). The bubbles help mix the medium 30, and also help purge the NO (that is formed in the medium 30) out into the exit gas stream of the nitric oxide generating system 12, 12'. This exit gas stream is shown as $N_2$/NO, and is a stream of nitrogen gas and nitric oxide gas.

The stream of nitrogen gas and nitric oxide gas $N_2$/NO exits the nitric oxide generating system 12, 12' through an outlet conduit 38. In other words, the outlet conduit 38 transports the stream of nitrogen gas and nitric oxide $N_2$/NO from the medium 30. The outlet conduit 38 may be a tube that has low or no permeability to at least the nitrogen gas and the nitric oxide. The length of the outlet conduit 38 may also be relatively short in order to avoid loss of gas before the stream is delivered to a desirable destination, such as a separator 42 (FIG. 2), a nitric oxide extraction device 44 (FIG. 4), or an oxygenator 46 (FIG. 5).

In some examples, the stream of nitrogen gas and nitric oxide gas $N_2$/NO stream may be transported as a result of pressure from the gas source, which may include a regulator to control the flow rate. In other examples, the stream of nitrogen gas and nitric oxide gas $N_2$/NO stream may be transported as a result of pressure from a vacuum positioned downstream.

As shown in FIGS. 1A and 1B, the gas delivery devices 10, 10' include an inspiratory gas conduit 40 operatively connected to the outlet conduit 38 to introduce an oxygen-containing gas OC and form an output gas stream OG of the gas delivery device 10, 10'. The oxygen-containing gas OC may be at least substantially pure oxygen gas $O_2$ or air. The oxygen-containing gas OC mixes with the stream of nitrogen gas and nitric oxide gas $N_2$/NO to form an output gas stream OG. In an example, the source (not shown) of the oxygen-containing gas OC may include a regulator to control the flow rate, so that the output gas stream OG contains from about 20% oxygen to about 99.99% oxygen. Since the oxygen-containing gas OC is introduced just prior to delivery to the recipient 48, the impact on the NO concentration is minimal or nil due to the short contact time between the NO and the oxygen-containing gas OC.

The inspiratory gas conduit 40 may be a tube that has low or no permeability to at least the oxygen-containing gas, the nitrogen gas, and the nitric oxide. Examples of suitable tubing material include poly(vinyl chloride) (PVC), polyurethane (PU), polyethylene (PE), fluorinated polymers, etc.

As will be discussed further in reference to FIGS. 2, 4A, 4B, and 5, examples of the method may also involve transporting the output gas stream OG to a desired destination. While not shown in FIGS. 1A and 1B, it is to be understood that the gas delivery devices 10, 10' may further include a delivery conduit 72 that is operatively connected to the outlet conduit 38 and the inspiratory gas conduit 40. As one example, the delivery conduit 72 may be connected to an exit of the outlet conduit 38 that is downstream of the inspiratory gas conduit 40 so that the gases have time to mix within the outlet conduit 38 before being delivered to the desired destination. Examples of other suitable connections for the delivery conduit 72 are described in reference to FIGS. 2, 4A, and 4B. The delivery conduit 72 may be a hose, tube, or other like conduit that can transport the output gas stream OG to the desired destination (e.g., to a patient through an inhalation unit that is operatively connected to the deliver conduit). The desired destination may be a patient 48 (FIGS. 2, 4A, and 4B) or a blood oxygenator 46 (FIG. 5).

Figure 2:
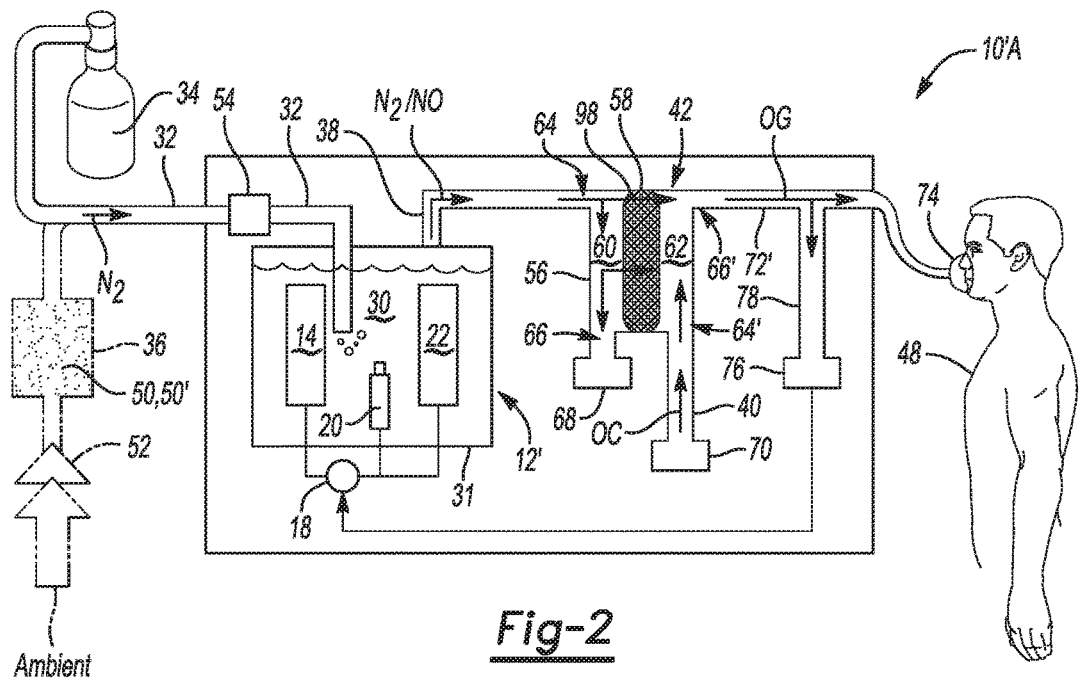
FIG. 2 is a schematic view of an example of a gas delivery device, including a nitric oxide generating system and a separator, being used for inhalation therapy.
Figure 4A:
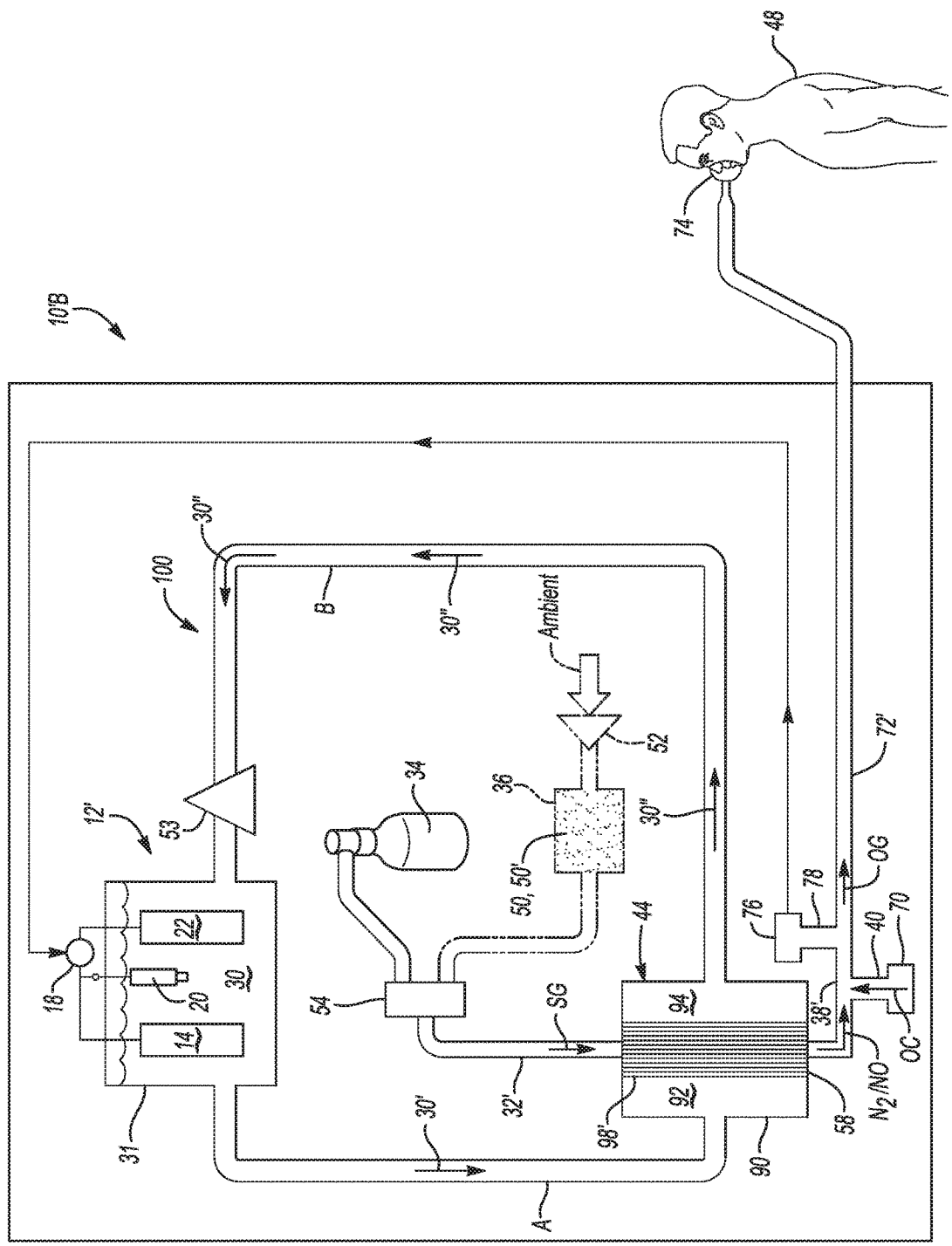
FIG. 4A is a schematic view of another example of a gas delivery device, including a nitric oxide generating system and a nitric oxide extraction device, being used for inhalation therapy.
Figure 4B:
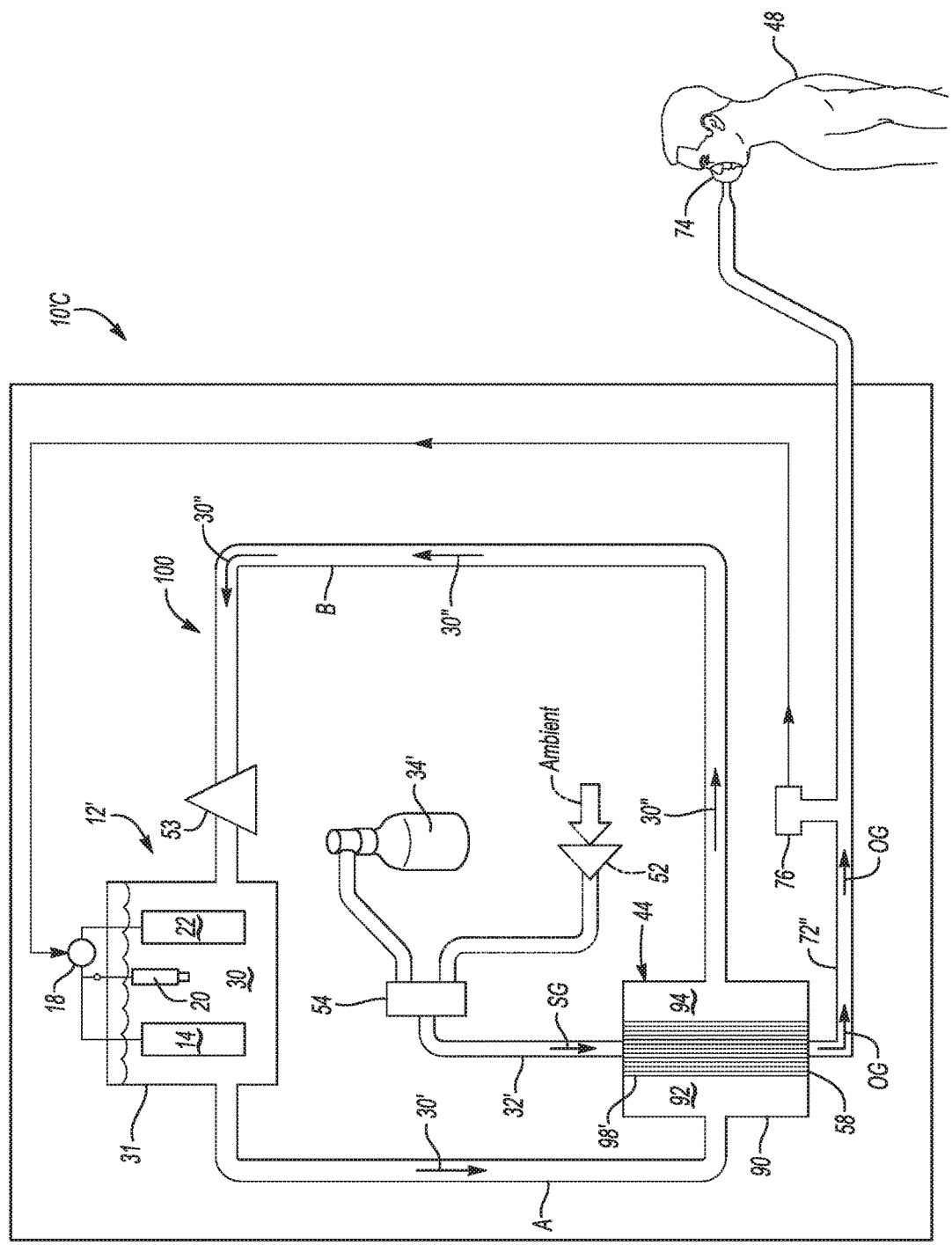
FIG. 4B is a schematic view of another example of a gas delivery device, including a nitric oxide generating system and a nitric oxide extraction device, being used for inhalation therapy.
Figure 5:
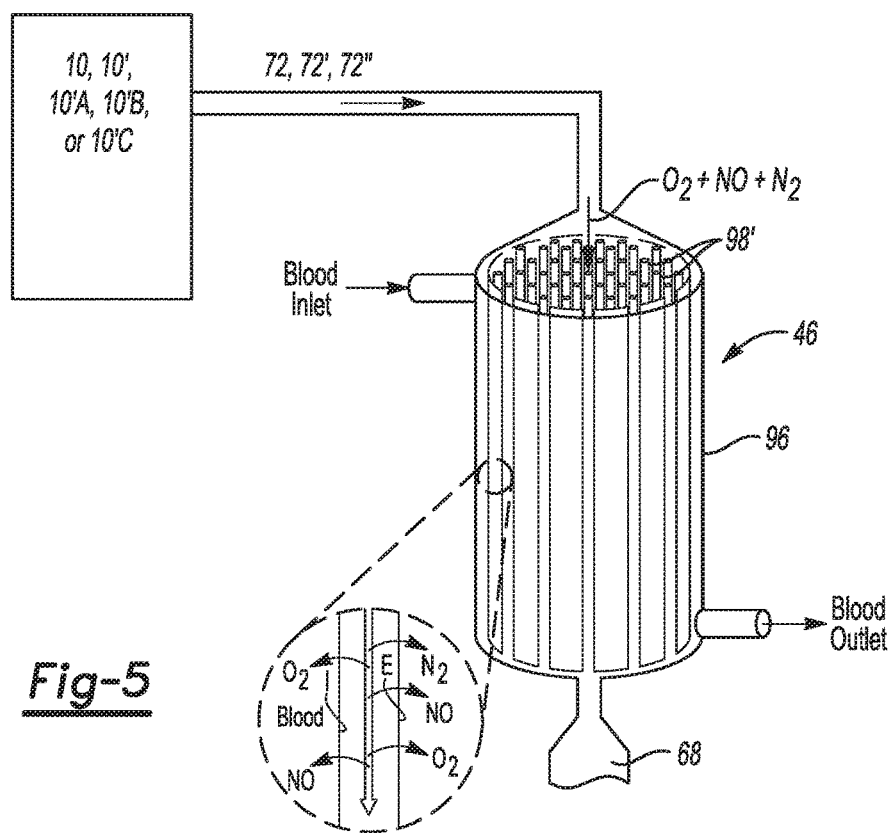
FIG. 5 is a schematic view of an example of a gas delivery device operatively connected to a blood oxygenator.

Different examples of the gas delivery device 10'A and 10'B (including the three-electrode nitric oxide generating system 12') for inhalation therapy are shown, respectively, in FIGS. 2, 4A, and 4B. It is to be understood that these devices could also be made with the two-electrode nitric oxide generating system 12. As shown in FIG. 5, any of the examples of the gas delivery device 10, 10', 10'A, 10'B, 10'C may be used to add nitric oxide to the sweep gas of a blood oxygenator 46, thereby helping to prevent platelet and other cell activation in the blood flowing through the oxygenator 46.

The potentiostat/galvanostat 18 and its associated electronics that are used in the examples shown in FIGS. 2, 4A, 4B, and 5 may be minimized to be secured to one or more components of the nitric oxide generating system 12' or another component of the gas delivery device 10, 10', 10'A, 10'B, and may be operated via a battery or another source of energy (e.g., solar generator, an energy harvesting device, etc.).

Referring now to FIG. 2, one example of the gas delivery device 10'A is shown for inhalation therapy. This example device 10'A includes the nitric oxide generating system 12', and each of its previously described components.

In this example device 10'A, the nitrogen gas $N_2$ may be supplied to the inlet conduit 32 from a gas source, such as the compressed gas tank 34 or the oxygen scrubber 36. Either the compressed gas tank 34 or the oxygen scrubber 36 may be used, and is operatively connected to the inlet conduit 32. The compressed gas tank 34 may include compressed nitrogen gas $N_2$, with a regulator to control the flow rate of the nitrogen gas $N_2$ to the inlet conduit 32. The oxygen scrubber 36 may be operatively connected to a pump 52 that introduces ambient air into the oxygen scrubber 36. The ambient air is directed to a solution or particle bed 50 of the oxygen scrubber 36, which is capable of removing the oxygen from the ambient air to generate the nitrogen gas $N_2$ that is delivered to the inlet conduit 32. As previously noted, the nitrogen gas $N_2$ may be a mixed gas derived from ambient air, where the mixed gas contains nitrogen gas, argon gas, carbon dioxide, and potentially small amounts of other non-oxygen gases. In an example, the oxygen scrubber removes at least 50% of the oxygen from the air, and thus the mixed gas may include less than 10% of oxygen gas. In another example, the oxygen scrubber removes enough oxygen from the air so that the mixed gas includes 5% or less of oxygen gas.

In this example of the device 10'A, the inlet conduit 32 delivers the nitrogen gas $N_2$ to the nitric oxide generating system 12', where NO has been electrochemically generated or will electrochemically generated in the manner previously described. The nitrogen purge gas $N_2$ may be introduced directly into the medium 30, or it may first pass through a flowmeter 54, which measures and controls the linear, nonlinear, mass or volumetric flow rate of the nitrogen purge gas $N_2$.

The nitrogen purge gas $N_2$ that is introduced into the system 12' picks up the nitric oxide that is generated in the medium 30. The resulting stream of nitrogen gas $N_2$ and nitric oxide $N_2$/NO is then transported out of the system 12' through the outlet conduit 38 as previously described.

It is to be understood that this gas stream $N_2$/NO may include some aerosol droplets, which contain the nitrite salt and, in some instances, the Cu(II)-ligand complex $Cu^{II}L$. In some instances, significant levels of aerosol droplets may be present, which is undesirable for various medical applications. The gas stream $N_2$/NO may be sent to a separator 42 that at least substantially removes the aerosol droplets.

The separator 42 may be operatively positioned between the outlet conduit 38 and the inspiratory gas conduit 40. This positioning of the separator 42 enables the aerosol droplets to be removed from gas stream $N_2$/NO before it is mixed with the oxygen-containing gas stream OC.

As shown in FIG. 2, the separator 42 includes a housing 56, which contains a nitric oxide permeable material 58 separating two spaces 60, 62. The housing 56 may be made of any material that is not permeable to the gases that are introduced thereto (e.g., nitrogen gas, nitric oxide, oxygen-containing gas).

The separator housing 56 includes two inlets 64, 64' and two outlets 66, 66'. The first housing inlet 64 operatively connects the outlet conduit 38 to the first space 60. As such, the gas stream $N_2$/NO is directed from the outlet conduit 38 into the first space 60. Once in the first space 60, the gas stream $N_2$/NO has two paths. Along the first path, some of the gas stream $N_2$/NO will diffuse across the nitric oxide permeable material 58 (also referred to herein as the nitric oxide permeable medium 58 ) into the second space 62. However, all of the gas stream $N_2$/NO cannot be forced through the nitric oxide permeable material 58. As such, the remainder of the gas stream $N_2$/NO will be transported along the second path, which leads to the first housing outlet 66 into a waste reservoir 68.

The gas stream $N_2$/NO that diffuses through the nitric oxide permeable material 58 has the aerosol droplets removed therefrom. The nitric oxide permeable material 58 may be a membrane ( 98 as shown in FIG. 2) or a bunch of hollow fibers ( 98' as shown in FIGS. 4A, 4B, and 5). The membrane 98 may be made up of several NO permeable microporous fibers (e.g., silicone rubber, porous polytetrafluoroethylene (PTFE), polybutadiene, poly(butadiene co-styrene), polycisisoprene, polypropylene (PP), etc.) or another material that allows some of the nitric oxide and some of the nitrogen gas $N_2$ to diffuse through to the second space 62 (i.e., performs the desired gas exchange). These fibers also block the aerosol droplets so that they are not transported through the membrane 98.

As mentioned above, the diffused gas stream N₂/NO (shown as D(N₂/NO) enters the second space 62 of the separator 42. The second space 62 is connected to the second housing inlet 64' and the second housing outlet 66'. The second housing inlet 64' is also operatively connected to the inspiratory gas conduit 40 to receive, in the second space 62, the oxygen-containing gas OC, which mixes with the nitric oxide diffusing through the nitric oxide permeable material 58 to form the output gas stream OG. The oxygen-containing gas OC may be delivered to the second space 62 from any suitable gas source 70, which can regulate the flow of the oxygen-containing gas OC or can be coupled to a flow controller to regulate the flow of the oxygen-containing gas OC. The flow rate of the oxygen-containing gas OC may be continuous or intermittent, and may also depend upon the composition of the oxygen-containing gas OC and the desired fraction of inspired oxygen (i.e., $FiO_2$). As example, the gas source 70 may be a compressed gas cylinder, a gas pump that delivers ambient air, or any other suitable gas source.

In the second space, diffused gas stream D(N₂/NO) mixes with the oxygen-containing gas OC to form the output gas stream OG.

A housing output conduit 72', which is an example of the previously mentioned delivery conduit 72, is operatively connected to the second housing outlet 66' to transport the output gas stream OG to a recipient/patient 48. The housing output conduit 72' may be any suitable polymeric or other tubing that is impermeable to the output gas stream OG. In an example, the housing output conduit 72' has a one-way valve so that the output gas stream OG does not flow back into the separator 42.

In the example shown in FIG. 2, an inhalation unit 74 may be connected to the housing output conduit 72' to deliver at least some of the output gas stream OG to the recipient/patient 48. The inhalation unit 74 may be a ventilator, a face mask, a nasal cannula, or some other suitable apparatus for delivering the output gas stream OG to the airways of the patient.

A sensor 76 may be positioned in contact with the output gas stream OG. The sensor 76 may be positioned in the housing output conduit 72', or in another conduit 78 that is split or branched off of the housing output conduit 72'. When the other conduit 78 is used, it receives at some of the output gas stream OG and transports it to the sensor 76. In some instances, it may be desirable to position the sensor 76 close to the gas source 70, where the oxygen-containing gas OC is introduced. In some other instances, it may be desirable to position the sensor 76 close to the inhalation unit 74 (e.g., within about 3 feet of the inhalation unit). While not shown, it is to be understood that in still other instances, the device 10'B may have two sensors 76, one close to the gas source 70 where the oxygen-containing gas OC is introduced, and another one close to the inhalation unit 74 (e.g., to ensure the stream entering the patient 48 has higher levels of NO and lower levels of $NO_2$).

The sensor 76 may be used to monitor the NO levels in the output gas stream OG. It may be desirable to monitor the NO level in order to avoid forming $NO_2$ (nitrogen dioxide, which can be generating from $O_2$ reacting with NO and can be toxic to the recipient/patient 48. Any suitable NO sensor 76 may be used.

In an example, the sensor 76 is a Shibuki-style sensor (not shown), which is based on the oxidation of NO to nitrate ($NO_3^-$) at an inner platinum (Pt) electrode position behind a gas permeable membrane.

Figure 3:
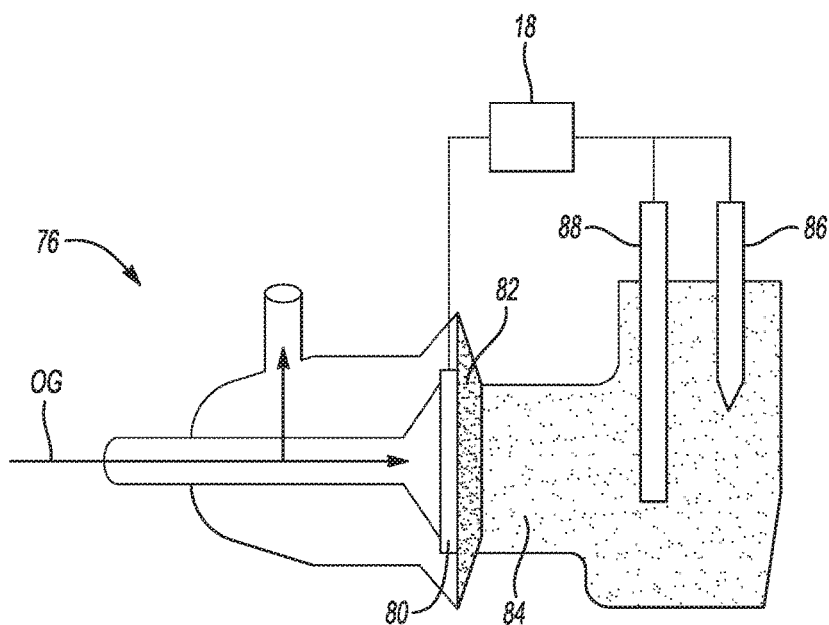
FIG. 3 is an example of a nitric oxide sensor that is suitable for use in any examples of the gas delivery device disclosed herein.

Another example of the sensor 76 is shown in FIG. 3. This sensor 76 is an amperometric NO sensor. The sensor 76 shown in FIG. 3 exhibits relatively rapid response times, and the high surface area of the working electrode(s) 80 yields larger currents than the Shibuki configuration.

As shown in FIG. 3, this example of the sensor 76 includes working electrode(s) 80 (e.g., platinum, gold, etc.) directly deposited (e.g., by chemical reduction) on the surface of a polymer electrolyte (i.e., ionomer film 82). Examples of the ionomer film 82 are a sulfonated tetrafluoroethylene based fluoropolymer-copolymer, such as NAFION® (from DuPont). This example of the sensor 76 also includes a reference electrode 86 and a counter electrode 88, which are immersed in an inner electrolyte solution 84 that also wets the ionomer phase 82.

The portion of the output gas stream OG transported through the conduit 78 flows over the surface of the working electrode(s) 80. A positive potential is applied (e.g., about 1V versus Ag/AgCl), and electrochemical reactions occur at the interface of the working electrode(s) 80 and the ionomer film 82. In an example, the positive potential applied to the working electrode(s) 80 ranges from about 0.7 V to about 1.1 V. A higher voltage may undesirably cause water oxidation. More specifically, the NO in the output gas stream OG electrochemically oxidizes to nitrite/nitrate to output current signals proportional to $NO_{(g)}$ levels.

In other examples, the sensor 76 can include another working electrode (not shown) on the same surface of the ionomer film 82 as the working electrode(s) 80, and a less positive potential may be applied to that other working electrode so that only $NO_2$ is oxidized (not NO) and sensed (via current measured). The NO sensor signal can be corrected for any $NO_2$ present using a bipotentiostat.

The sensor 76 data (i.e., the concentration of NO in the output gas stream OG and/or the concentration of $NO_2$ in the output gas stream OG) may be used to servo-regulate the potential or current applied to the NO generating system 12, 12' to achieve an at least substantially constant concentration of NO at the delivery end. The data may also be used to regulate the flow of the output gas stream OG.

When the sensor 76 data indicates that the NO level is too high or too low, the applied potential or current may be adjusted and/or the flow rate of one or more of the gases may be adjusted. In an example of the method, the sensor 76 monitors a nitric oxide level of the output gas stream OG, and based on the nitric oxide level of the output gas stream OG, the potentiostat/galvanostat 18 one of: maintains the applied cathodic voltage or current (e.g., when the NO is at a desired level); or adjusts the applied cathodic voltage or current to increase NO production (e.g., when the nitric oxide level of the output gas stream OG is below a target level); or adjusts the applied cathodic voltage or current to decrease NO production (e.g., when the nitric oxide level of the output gas stream OG is above the target level). When the sensed NO level is too low, a more negative potential (that is also more positive than the cathodic potential that causes water reduction) or an increased cathodic current (that is below a limiting current) may be applied. When the sensed NO level is too high, a less negative (i.e., more positive) potential or a decreased cathodic current may be applied. As an example, the voltage may be modulated to be more or less negative in order to increase or decrease, respectively, the rate of NO production, and thus the flux of NO swept from the NO generating device 12, 12' and present in the output gas stream OG.

The target level may be based upon the given application in which the NO is being used. The target level may be very low or very high, depending upon the patient and the application. As examples, the target level of NO for a newborn on inhalation therapy may range from about 10 ppm to about 70 ppm, and the target level of NO to be generated in an oxygenator to prevent activation of platelets and other cells during bypass surgery may range from about 190 ppm to about 210 ppm. Further, for antimicrobial applications, such as for lung infections, lower levels of NO may be useful for inhalation therapy, in the range of, for example, from about 500 ppb to about 10 ppm.

The sensor 76 data may be used to determine whether a modulation in the flux of the generated NO is desirable. Several techniques may be used to modulate the flux, including altering an amount of a surface area of the working electrode 14 that is exposed to the medium 30, and/or altering a concentration of any of the Cu(II)-ligand complex $Cu^{II}L$ or the source of nitrite ions, and/or altering a magnitude of the cathodic voltage over time (as previously described), and/or altering a magnitude of the cathodic current over time (as previously described). Increasing the surface area of the working electrode 14 will increase the NO production rate, while decreasing the surface area of the working electrode 14 will decrease the NO production rate. In some examples, the concentration of the Cu(II)-ligand complex $Cu^{II}L$ may be varied from about 1 mM to about 10 mM and/or the concentration of the source of nitrite ions may be varied from about 50 mM to about 1 M. Increasing the concentrations of both the Cu(II)-ligand complex $Cu^{II}L$ and the source of nitrite ions is expected to increase the NO production rate, while decreasing the concentrations of both the Cu(II)-ligand complex $Cu^{II}L$ and the source of nitrite ions is expected to decrease the NO production rate. When altering the magnitude of the cathodic voltage, more negative potentials (before reaching limiting current) should increase the NO production rate. When altering the magnitude of the cathodic current, higher current (but below limiting current) should increase the NO production rate.

The sensor 76 data may also be used to determine whether an undesirable amount of $NO_2$ is present in the output gas stream OG. If an undesirable amount of $NO_2$ is present, an alarm on the device 10'A may be initiated and/or the applied voltage and/or current may be adjusted to reduce the NO delivery from the system 12'. Moreover, a soda lime scrubber may be included in the inhalation unit 74, just before the output gas stream OG is delivered to the patient 48. If the $NO_2$ content is greater than 1 ppm in the final gas phase, the soda lime scrubber can remove the excess $NO_2$.

Referring now to FIGS. 4A and 4B, two examples of the gas delivery device 10'B and 10'C for inhalation therapy are respectively depicted. Each example device 10'B, 10'C includes the nitric oxide generating system 12', and each of its previously described components. Each example device 10'B, 10'C also includes a nitric oxide extraction device 44 (the components of which are described below), and a fluid recirculation system 100 connecting the housing 31 of the nitric oxide generating system 12' to a housing 90 of the nitric oxide extraction device 44.

In these examples, the nitric oxide is electrochemically generated in the solution 30 as previously described. The solution 30', which has dissolved electrochemically generated nitric oxide therein, is then circulated through a fluid recirculation system 100 to a nitric oxide extraction device 44 for extraction of the nitric oxide from the solution 30'. The fluid recirculation system 100 fluidly connects the nitric oxide generating system 12' to the nitric oxide extraction device 44. As used herein, the term "fluidly connect," means that two spatial regions are connected together such that a liquid (and any gas(es) dissolved therein) may flow between the two spatial regions. As an example, a first conduit A of the fluid recirculation system 100 fluidly connects an outlet in the housing 31 of the nitric oxide generating system 12' to an inlet of a housing 90 of the nitric oxide extraction device 44.

The nitric oxide extraction device 44 may be operatively positioned along the fluid recirculation system 100. As shown in FIGS. 4A and 4B, the nitric oxide extraction device 44 includes the housing 90, which contains a nitric oxide permeable material/medium 58 positioned therein. The housing 90 may be made of any material that is not permeable to the gases that are introduced thereto (e.g., nitrogen gas, nitric oxide and/or oxygen-containing gas).

Within the housing 90, a space at least partially surrounds the nitric oxide permeable material 58. The space includes an input area 92. The input area 92 receives the nitric oxide-containing solution 30' from the nitric oxide generating system 12' through the first conduit A of the fluid recirculation system 100. As used herein, the phrase "nitric oxide-containing solution" refers to the medium/solution having the generated nitric oxide dissolved therein. The space also includes an output area 94. The output area 94 transports an at least substantially reduced nitric oxide solution 30 " out of the nitric oxide extraction device 44 through a second conduit B of the fluid recirculation system 100. As used herein, the phrase "at least substantially reduced nitric oxide-containing solution" refers to the medium/solution after at least some of the nitric oxide removed therefrom, and thus the concentration of NO in the at least substantially reduced nitric oxide-containing solution 30" is less than the concentration of NO in the nitric oxide-containing solution 30'. As such, both solutions 30', 30" include the source of nitrite ions, and in some instances, the Cu(II)-ligand complex $Cu^{II}L$ (i.e., when it is in the medium 30 and not immobilized on the working electrode 14), but solution 30" includes less nitric oxide than the solution 30'.

The nitric oxide-containing solution 30' is directed from a conduit A of the fluid recirculation system 100 into the input area 92. Once in the input area 92, at least some of the nitric oxide will diffuse out of the solution 30' and across the nitric oxide permeable material 58. The remaining solution 30" (which now has a lower nitric oxide concentration) will be transported/circulated on the outside of the nitric oxide permeable material 58, which leads to the output area 94 and into the other conduit B of the fluid recirculation system 100.

The conduit B of the fluid recirculation system 100 connects an outlet of the housing 90 to an inlet of the housing 31 of the nitric oxide generating system 12'. A pump 53 may be operatively connected along the conduit B. An example of the pump 53 is a centrifugal type pump. The pump 53 enables the solution 30' to transport, in a single direction, through the first conduit A into the nitric oxide extraction device 44 and enables the at least substantially reduced nitric oxide solution 30" to transport, in the single direction, through the second conduit B and into the nitric oxide generating system 12'. The pump 53 may circulate the medium, 30', 30" at a liquid flow rate ranging from about 170 mL/min to about 535 mL/min. The nitric oxide solution 30 " may be reused in the nitric oxide generating system 12' to generate additional NO and form the solution 30'. The conduits A and B may be any of the gas impermeable materials disclosed herein.

The nitric oxide that diffuses through the nitric oxide permeable material 58 is separated from the remainder of the solution 30". In this example, the nitric oxide permeable material 58 may be a bunch of hollow fibers 98'. Each hollow fiber 98' may be made up of silicone rubber, porous polytetrafluoroethylene (PTFE), polybutadiene, poly(butadiene co-styrene), polycisisoprene, polypropylene (PP), or another material that allows some of the nitric oxide to diffuse therethrough.

In these examples, the nitric oxide extraction device 44 includes an inlet conduit 32' that delivers a sweep gas SG to the nitric oxide permeable material 58. The sweep gas SG is selected from the group consisting of nitrogen gas $N_2$, an oxygen-containing gas, and combinations thereof. The nitric oxide extraction device 44 also includes an outlet conduit 72' or 72" that transports a mixed gas stream from the nitric oxide permeable medium 58. The mixed gas stream includes nitric oxide and the sweep gas SG. As such, in some examples the mixed gas includes $N_2$/NO as shown in FIG. 4A, and in other examples, the mixed gas includes the output gas stream OG as shown in FIG. 4B.

In the example device 10'B shown in FIG. 4A, the nitrogen gas $N_2$ is the sweep gas SG that is delivered to the nitric oxide permeable material 58. Similar to the device 10'A, the nitrogen gas $N_2$ in this example device 10'B may be supplied to the inlet conduit 32' from a gas source, such as the compressed gas tank 34 or the oxygen scrubber 36. Either the compressed gas tank 34 or the oxygen scrubber 36 may be used, and is operatively connected to the inlet conduit 32'. The compressed gas tank 34 may include compressed nitrogen gas $N_2$, with a regulator to control the flow rate of the nitrogen gas $N_2$ to the inlet conduit 32. The oxygen scrubber 36 may be operatively connected to a pump 52 that introduces ambient air into the oxygen scrubber 36. The ambient air is directed to a solution or particle bed 50 of the oxygen scrubber 36, which is capable of removing the oxygen from the ambient air to generate the nitrogen gas $N_2$ that is delivered to the inlet conduit 32'. As previously noted, the nitrogen gas $N_2$ may be a mixed gas derived from ambient air, where the mixed gas contains nitrogen gas, argon gas, carbon dioxide, and potentially small amounts of other non-oxygen gases, or may be a mixture of nitrogen gas and other inert gas(es).

In this example of the device 10'B shown in FIG. 4A, the inlet conduit 32' delivers the nitrogen gas $N_2$ to the nitric oxide permeable material 58, where NO (diffused from the solution 30') is crossing the fibers 98'. The nitrogen purge gas $N_2$ may be introduced directly into the nitric oxide permeable material 58, or it may first pass through a flowmeter 54, which measures and controls the linear, nonlinear, mass or volumetric flow rate of the nitrogen gas $N_2$.

The nitrogen gas $N_2$ that is introduced into the nitric oxide extraction device 44 picks up the nitric oxide that is crossing the nitric oxide permeable material 58. The resulting stream of nitrogen gas $N_2$ and nitric oxide $N_2$/NO is then transported out of the nitric oxide extraction device 44 through the outlet conduit 38'.

It is to be understood that this gas stream $N_2$/NO includes no solution 30', as the fibers 98 block the solution 30' so that it is not transported through the material 58.

The outlet conduit 38' is also operatively connected to the inspiratory gas conduit 40 to receive the oxygen-containing gas OC, which mixes with the gas stream $N_2$/NO to form the output gas stream OG. The oxygen-containing gas OC may be delivered from any suitable gas source 70 (e.g., compressed gas cylinder, gas pump that delivers ambient air, etc.), which can regulate the flow of the oxygen-containing gas OC or can be coupled to a flow controller to regulate the flow of the oxygen-containing gas OC. The flow rate of the oxygen-containing gas OC may be continuous or intermittent, and may also depend upon the composition of the oxygen-containing gas OC and the desired fraction of inspired oxygen (i.e., $FiO_2$).

In the outlet conduit 38', the gas stream $N_2$/NO mixes with the oxygen-containing gas OC to form the output gas stream OG.

A delivery conduit 72' is operatively connected to the outlet conduit 38' to transport the output gas stream OG to a recipient/patient 48. The delivery conduit 72' may be any suitable polymeric or other tubing that is impermeable to the output gas stream OG. In an example, the delivery conduit 72' has a one-way valve so that the output gas stream OG does not flow back into the nitric oxide extraction device 44. It is to be understood that the delivery conduit 72' and the outlet conduit 38' of FIG. 4A may be separate tubes that are operatively connected to one another, or may be a single tube.

In the example device 10'C shown in FIG. 4B, the oxygen-containing gas OC (i.e., $O_2$ or ambient air) is the sweep gas SG that is delivered to the nitric oxide permeable material 58. In this example, the oxygen-containing gas OC may be delivered from any suitable gas source (e.g., compressed gas cylinder 34', gas pump 52 that delivers ambient air, etc.), which can regulate the flow of the oxygen-containing gas OC or can be coupled to a flow controller to regulate the flow of the oxygen-containing gas OC into the inlet conduit 32'. In an example, 100% air saturation may be used, which corresponds to about 10 mg/L (ppm) of $O_2$ in the output gas stream OG.

In this example, the oxygen-containing gas OC alone may be used, or it may be mixed with the nitrogen gas $N_2$. While not shown, it is to be understood that when the nitrogen gas $N_2$ is introduced with the oxygen-containing gas OC, the gas delivery device 10'C may also include a compressed gas tank 34 introduces the nitrogen gas $N_2$ into the inlet conduit 32'.

In this example of the device 10'C shown in FIG. 4B, the inlet conduit 32' delivers the oxygen-containing gas OC to the nitric oxide permeable material 58, where NO (diffused from the solution 30') is crossing the fibers 98'. In this example, the oxygen-containing gas OC acts as the purge gas, and may be introduced directly into the nitric oxide permeable material 58, or it may first pass through a flowmeter 54, which measures and controls the linear, nonlinear, mass or volumetric flow rate of the oxygen-containing gas OC.

The oxygen-containing gas OC that is introduced into the nitric oxide extraction device 44 picks up the nitric oxide that is crossing the nitric oxide permeable material 58. In this example, the resulting gas stream is the output gas stream OG because it contains nitric oxide and the oxygen-containing gas OC (with or without the nitrogen gas $N_2$). It is to be understood that output gas stream OG includes no solution 30', as the fibers 98' block the solution 30' so that it is not transported through the material 58.

The output gas stream OG is then transported out of the nitric oxide extraction device 44 through the delivery conduit 72" (which in this example is the outlet conduit 38').

Since the oxygen-containing gas OC is introduced as the purge gas in this example, the gas delivery device 10'C does not include the inspiratory gas conduit 40 or the gas source 70 operatively connected to the delivery conduit 72".

The delivery conduit 72" is capable of transporting the output gas stream OG to a recipient/patient 48. The delivery conduit 72" may be any suitable polymeric or other tubing that is impermeable to the output gas stream OG. In an example, the delivery conduit 72" has a one-way valve so that the output gas stream OG does not flow back into the nitric oxide extraction device 44.

In the example shown in FIGS. 4A and 4B, an inhalation unit 74 may be connected to the respective delivery conduit 72', 72" to deliver at least some of the output gas stream OG to the recipient/patient 48. The inhalation unit 74 may be a ventilator, a face mask, a nasal cannula, or some other suitable apparatus for delivering the output gas stream OG to the airways of the patient.

The sensor 76 may be positioned in contact with the output gas stream OG. The sensor 76 may be positioned in the delivery conduit 72', 72", or in another conduit 78 that is split or branched off of the delivery conduit 72', 72". When the other conduit 78 is used, it receives at some of the output gas stream OG and transports it to the sensor 76. In some instances, it may be desirable to position the sensor 76 close to the inhalation unit 74 (e.g., within about 3 feet of the inhalation unit). The sensor 76 may be used to monitor the NO levels in the output gas stream OG in the same manner as previously described. The data from the sensor 76 may be used to adjust the applied potential or current and/or the flow rate of one or more of the gases.

In the examples shown in FIGS. 2 and 4A, the gas stream $N_2$/NO may have NO ranging from about 100 ppmv to about 400 ppmv. In the examples shown in FIGS. 2, 4A, and 4B, the output gas stream OG (including the oxygen-containing gas OC) may have NO levels ranging from about 0.1 ppmv to about 400 ppmv.

Referring now to FIG. 5, any example of the gas delivery device 10, 10', 10'A, 10'B, 10'C is shown as part of an oxygenator 46. The output gas stream OG may be generated as previously described and may be transported to the conduit 72, 72', 72". The length of the conduit 72, 72', 72" may be relatively short in order to avoid loss of gas before the stream is delivered to the oxygenator 46.

The conduit 72, 72', 72" is configured to transport the output gas stream OG of oxygen gas, nitrogen gas and nitric oxide or oxygen gas and nitric oxide from the gas delivery device 10, 10', 10'A, 10'B, 10'C to an oxygenator 46, which includes the hollow fibers 98', which are capable of filtering and cleaning the gas stream OG. In this particular example, the oxygenator 46 is a blood oxygenator, which includes a housing 96 with a blood inlet, a blood outlet, a gas inlet, and a gas outlet (leading to waste 68 ).

The gas inlet of the housing 96 is operatively connected to the conduit 72, 72', 72 ". More particularly, the gas inlet directs the output gas stream OG from the conduit 72, 72', 72" into fibers 98' that are contained within the housing 96. In this example, each fiber 98' is a hollow polymeric fiber having a first or interior surface I and a second or exterior surface E. A single blood oxygenator housing 96 may include thousands of hollow polymeric fibers. The output gas stream OG is introduced adjacent to the first or interior surface I. The walls of the hollow polymer fibers act as filters, allowing only the oxygen-containing gas, in some instances the nitrogen gas, and the nitric oxide from the output gas stream OG to permeate therethrough (while trapping contaminants therein). As such, the cleaned output gas stream OG exits from the second or exterior surface E into any blood contained within the housing 96 (as shown in the expanded portion of FIG. 5). Any of the cleaned output gas stream OG that does not exit into the blood will be directed to the waste reservoir 68.

The NO in this example serves to locally prevent platelet adhesion and activation on the second or exterior surface E of the fibers 98. NO coming through the fibers 98 of the oxygenator 46 into the blood can also inhibit activation of white blood cells. The effect of the NO is localized since it reacts immediately with oxyhemoglobin to form met-hemoglobin. When the blood exits the oxygenator 46, NO is no longer present in the cleaned stream. As such, the blood, containing a cleaned stream of oxygen gas and potentially nitrogen gas $N_2$, can then exit the housing 46 and be delivered to a patient 48 (not shown in FIG. 5).

It is to be understood that various other configurations may be utilized, for example, the blood oxygenator 46 may have a different design.

While several examples of the gas delivery device 10, 10', 10'A, 10'B, 10'C are depicted, it is to be understood that various other configurations may be utilized. For example, a single polymer tube may form the inlet conduit 32 and the outlet conduit 38, and may be positioned within the medium 30 where NO is generated. In this example, the polymer tube would be permeable to the NO, and the stream of nitrogen gas $N_2$ transported through the tube would pick up the NO through the permeable tube (i.e., NO would diffuse through the polymer tubing and join the gas stream).

In the examples of the method disclosed herein, the cathodic voltage or cathodic current may be applied to the working electrode 14 for any time interval up to, for example, 30 days. In some instances, it is believed that the voltage or current may be applied continuously for even longer than 30 days. When it is desired to stop generating NO, the cathodic voltage or current is no longer applied to the electrode 14. The NO release lifetime may be longer when larger reservoir volumes of the medium 30 are used, when higher concentrations of the source of nitrite ions are used, and/or when greater NO conversion efficiency is achieved.

Also in the examples of the method disclosed herein, any suitable gas flow rate may be used. As an example, the flow rate of the nitrogen gas $N_2$ and/or the oxygen-containing gas OC may range from about 50 mL/min to about 5 L/min.

To further illustrate the present disclosure, examples are given herein. It is to be understood that these examples are provided for illustrative purposes and are not to be construed as limiting the scope of the present disclosure.

EXAMPLES

Example 1

Figure 6:
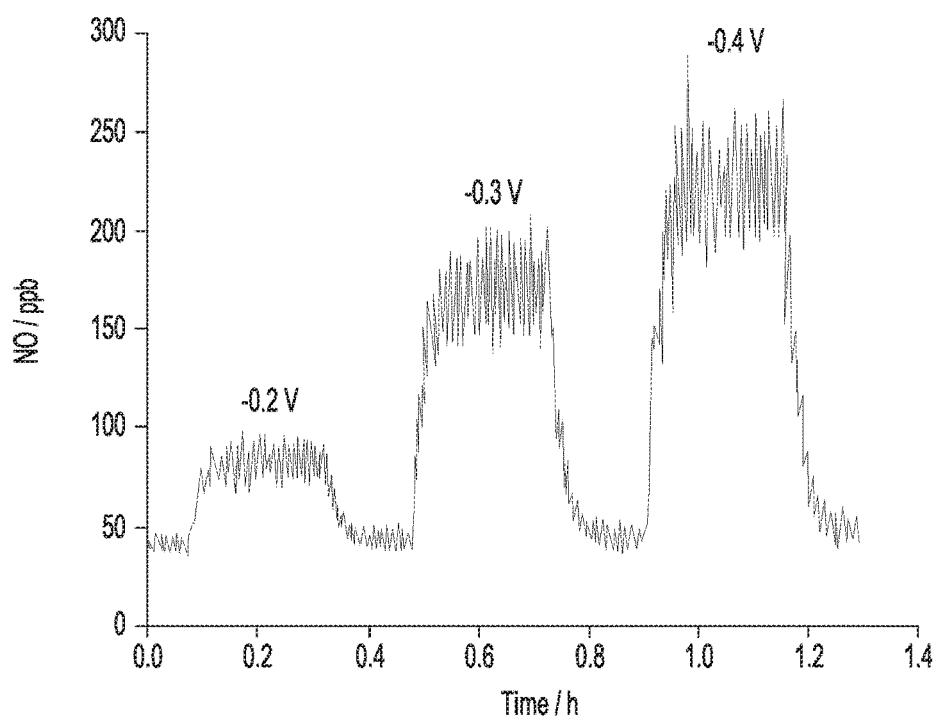
FIG. 6 is a graph depicting the modulation of nitric oxide generation, in terms of the NO ppb level versus time (in hours), in a bulk aqueous solution of 2 mM Cu(II)-tri(2-pyridylmethyl)amine (CuTPMA), 100 mM sodium nitrite, and 0.1 M 3-(N-morpholino)propanesulfonic acid (MOPS) buffer by applying −0.2 V, −0.3 V, and −0.4 V (versus a 3 M Cl$^-$ Ag/AgCl reference electrode) on a 0.071 cm$^2$ glassy carbon electrode.

An aqueous medium was prepared with 2 mM Cu(II) TPMA, 100 mM sodium nitrite and 0.1 M MOPS buffer (the solution was buffered to pH 7.2). The NO was generated by applying a particular voltage for a particular time. The working electrode was a 0.071 cm$^2$ glassy carbon electrode, the counter electrode was a platinum wire, and the reference electrode was Ag/AgCl. The modulation of NO generation was performed by applying −0.2 V, then −0.3 V, then −0.4 V (vs. 3 M Cl$^-$ Ag/AgCl reference electrode). The solution was bubbled with $N_2$ to purge the NO produced. The resulting gas phase was analyzed for NO content using chemiluminescence. The results are shown in FIG. 6. These results illustrate that by applying different cathodic potentials to the working electrode, different levels of NO in the gas phase can be produced even with a small area working electrode. The higher cathodic voltage yielded higher gas phase NO levels.

Example 2

Figure 7:
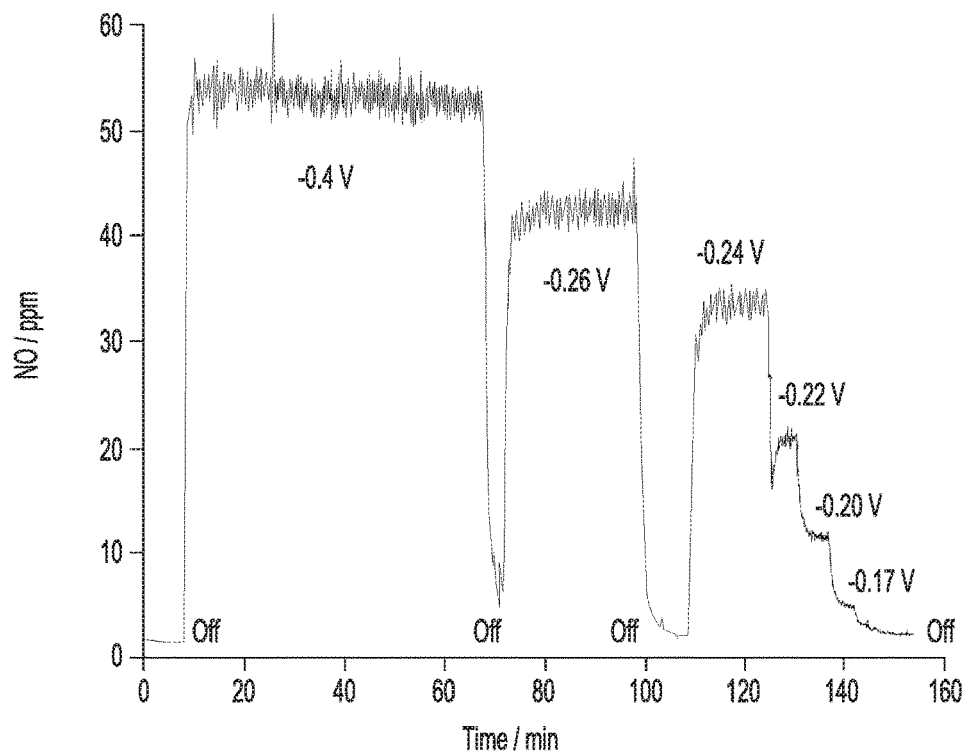
FIG. 7 is a graph depicting the modulation of nitric oxide generation, in terms of the NO ppm level versus time (in minutes), in a bulk aqueous solution of 2 mM CuTPMA, 400 mM sodium nitrite, and 0.2 M 4-(2-hydroxyethyl)-1-piperazineethanesulfonic acid) (HEPES) buffer (pH 7.2) by applying −0.4 V, −0.26 V, −0.24 V, −0.22 V, −0.20 V, and −0.17 V (versus a 3 M Cl$^-$Ag/AgCl reference electrode) on a gold mesh electrode of about 15 cm$^2$.

An aqueous medium was prepared with 2 mM Cu(II) TPMA, 0.4 M sodium nitrite and 0.2 M HEPES buffer (the solution was buffered to pH 7.2). The NO was generated by applying a particular voltage for a particular time. The working electrode had a larger area than the working electrode used in Example 1. In particular, the working electrode was a 2.5×3.5 cm gold mesh electrode (i.e., active surface of about 15 cm$^2$), the counter electrode was a large (~25 cm$^2$) platinum mesh electrode, and the reference electrode was Ag/AgCl. The modulation of NO generation was performed by applying −0.4 V, then −0.26 V, then −0.24 V, then −0.22 V, then −0.20 V, then −0.17 V (all vs. 3 M Cl$^-$ Ag/AgCl reference electrode), and then the potential was turned off. The solution was bubbled with N$_2$ (at a rate of 0.2 L/min) to purge the NO produced. The resulting gas phase was analyzed for NO content using chemiluminescence. The results are shown in FIG. 7. When comparing FIGS. 6 and 7, much higher levels of NO were generated when using the larger area working electrode. The results with the larger area working electrode also illustrate that by applying different cathodic potentials to the working electrode, different levels of NO in the gas phase can be produced, and that higher cathodic voltages yield higher gas phase NO levels.

Example 3

Figure 8:
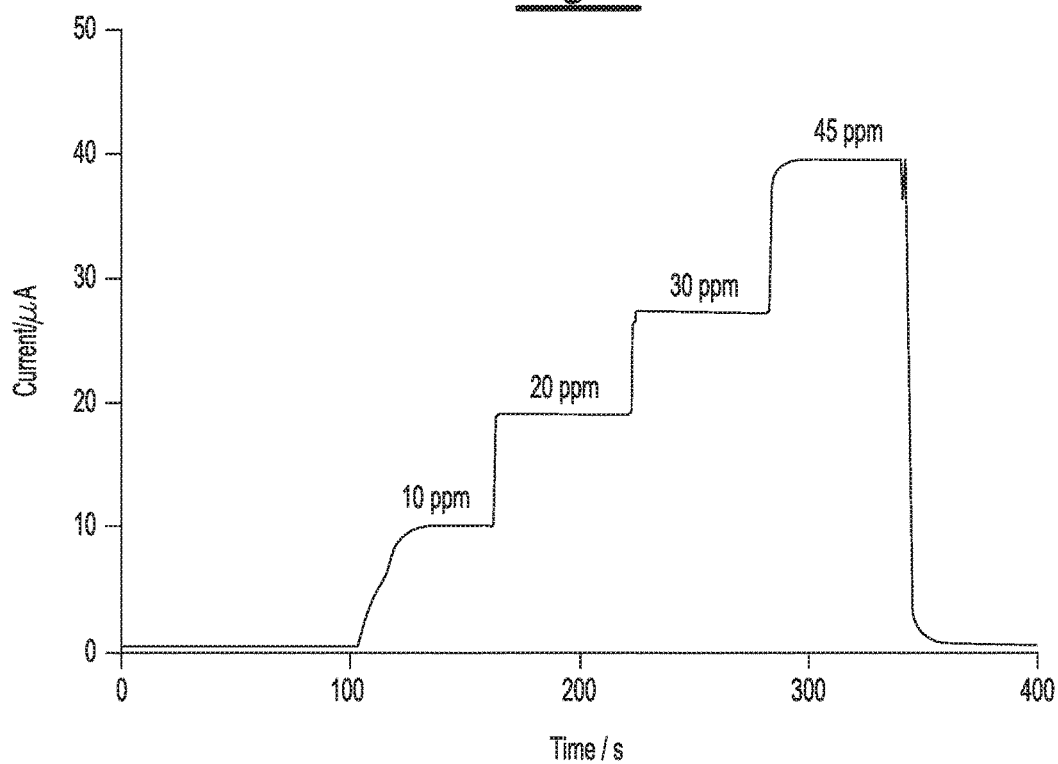
FIG. 8 is a graph depicting the amperometric gas phase responses, in terms of current (μA) versus time (in seconds), of an example sensor disclosed herein to NO$_{(g)}$ levels generated and swept in a nitrogen gas stream.

The NO levels were detected using an amperometric sensor similar to the one shown in FIG. 3. The sensor included a gold working electrode deposited on a NAFION® membrane (i.e., the ionomer phase). The generated gas stream (including NO) was directed over the surface of the working electrode, and the electrochemical oxidation of NO occurred at the interface of the metal working electrode and the ionomer phase which was wetted from an inner electrolyte solution (0.5 M H$_2$SO$_4$). This sensor exhibited rapid response to the gas phase NO, as shown in FIG. 8), with a linear response from 5 ppbv-600 ppmv NO.

Example 4

Figure 9:
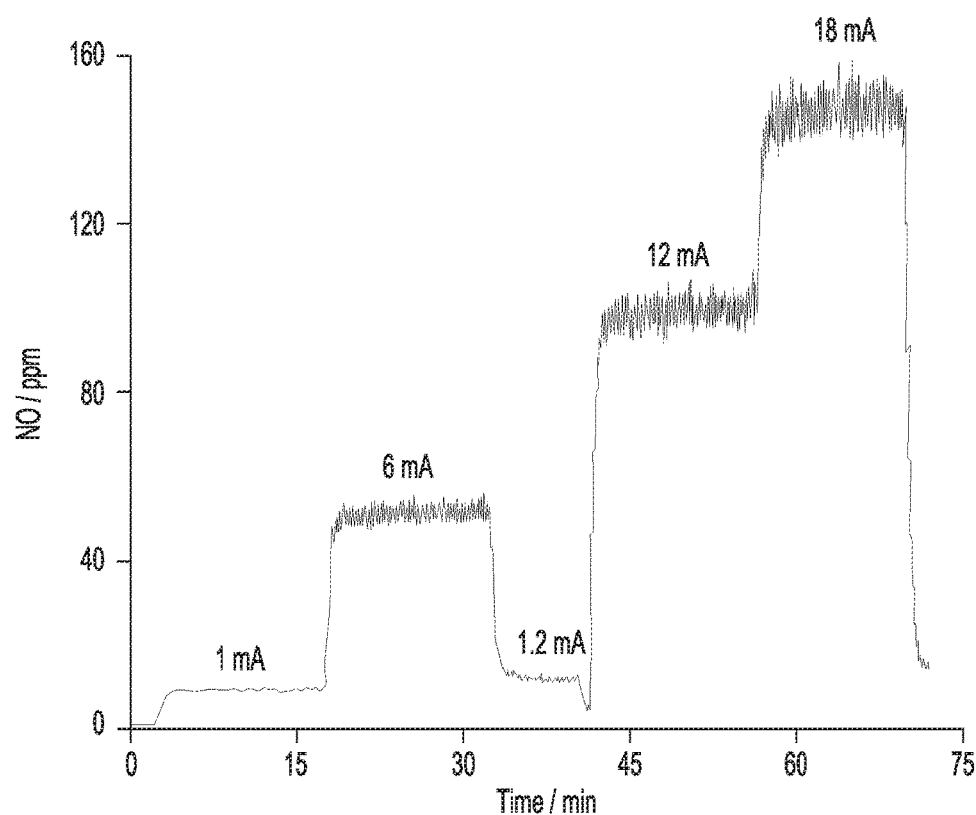
FIG. 9 is a graph depicting the modulation of nitric oxide generation, in terms of the NO ppm level versus time (in minutes), in a bulk aqueous solution of 7 mM Cu(II)-1,4,7-trimethyl-1,4,7-triazacyclononane (CuMe$_3$TACN), 1 M sodium nitrite, and 0.5 M HEPES buffer (pH 7.3) using a constant current method on a 25 cm$^2$ platinum mesh electrode.

An aqueous medium was prepared with 7 mM Cu(II) Me$_3$TACN, 1 M sodium nitrite and 0.5 M HEPES buffer (the solution was buffered to pH 7.3). The NO was generated by applying constant voltages at different times. The working electrode was a 25 cm$^2$ gold mesh electrode, the counter electrode was platinum, and the reference electrode was Ag/AgCl. The modulation of NO generation was performed by continuously adjusting the voltage to apply constant currents of 1 mA, 6 mA, 1.2 mA, 12 mA, and 18 mA for different time periods. The solution was bubbled with N$_2$ (at a rate of 1 L/min) to purge the NO produced. The resulting gas phase was analyzed for NO content using chemiluminescence. The results are shown in FIG. 9. As illustrated, higher levels of NO were generated when the current was increased. The results also indicate that a substantially constant level of NO can be generated with the constant current method.

Example 5

Figure 10A:
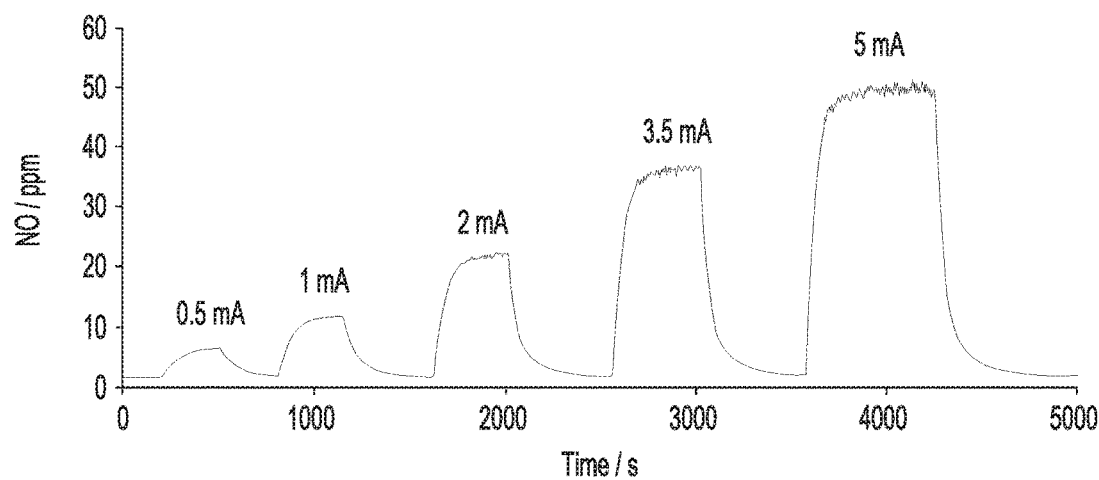
FIG. 10A is a graph depicting the modulation of nitric oxide generation, in terms of the NO ppm level versus time (in seconds), in an output gas stream containing 20% oxygen, where the NO was generated from a bulk aqueous solution of 7 mM CuMe$_3$TACN, 1 M sodium nitrite, and 0.5 M HEPES buffer (pH 7.3) using a constant current method on a 25 cm$^2$ platinum mesh electrode.
Figure 10B:
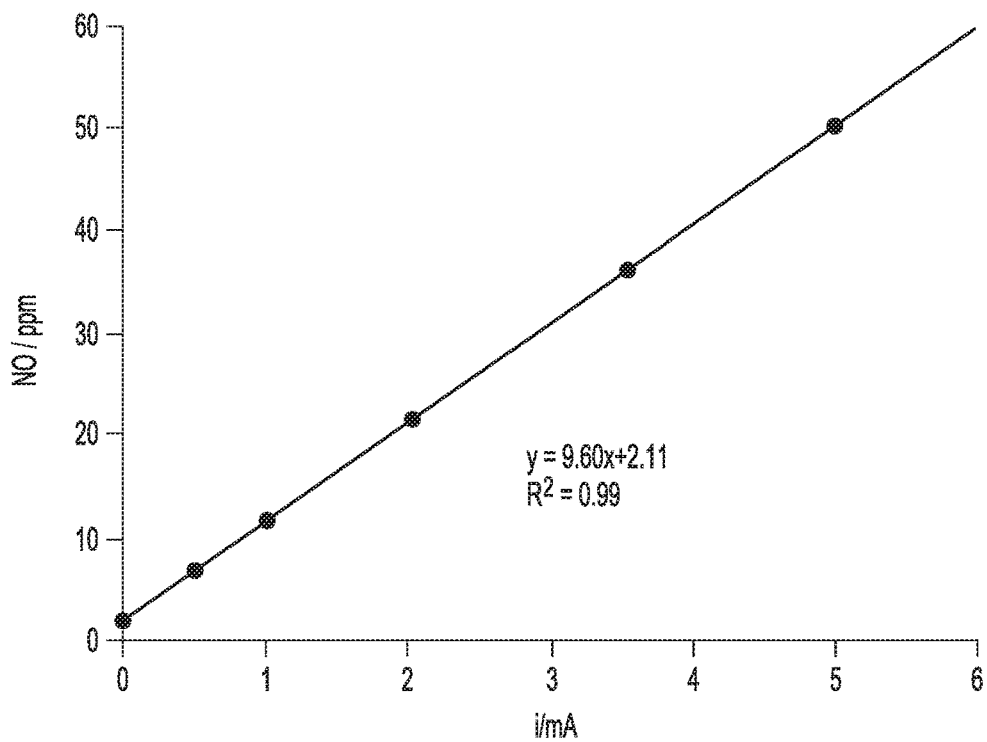
FIG. 10B is a graph depicting the NO generation of FIG. 10A in terms of NO ppm level versus the applied current (mA)

An aqueous medium was prepared with 7 mM Cu(II) Me$_3$TACN, 1 M sodium nitrite and 0.5 M HEPES buffer (the solution was buffered to pH 7.3). The NO was generated by applying constant currents at different times. The working electrode was a 25 cm$^2$ gold mesh electrode, the counter electrode was platinum, and the reference electrode was Ag/AgCl. The modulation of NO generation was performed by continuously adjusting the voltage to apply constant currents of 0.5 mA, 1 mA, 2 mA, 3.5 mA, and 5 mA for different time periods. The solution was bubbled with N$_2$ (at a rate of 1 L/min) to purge the NO produced. A constant steam of 20% oxygen was added to the N$_2$/NO gas stream. The resulting gas phase was analyzed for NO content using chemiluminescence. The results are shown in FIG. 10A. As illustrated, higher levels of NO were generated when the current was increased. The results also indicate that a substantially constant level of NO can be generated with the constant current method. In FIG. 10B, the NO measurements are plotted versus the current that was applied. As illustrated, about 9.6 ppm of NO was released for every 1 mA of applied current.

Example 6

Aqueous solutions were prepared with 7 mM Cu(II) Me$_3$TACN, 1 M sodium nitrite and 0.5 M HEPES buffer (the solution was buffered to pH 7.3). The working electrode was a 4.5×8.5 cm$^2$ gold mesh electrode, and the reference/counter electrode was a 4×4 cm$^2$ gold electrode. The generation of NO and the modulation of NO generation were performed by continuously adjusting the voltage to apply constant currents of 5 mA, 10 mA, 20 mA, and/or 30 mA for different time periods.

The solution containing the generated NO was pumped into a fiber bundle, where NO diffused through the fibers and excess solution was recirculated back into the container used for NO generation. Air was introduced into the fiber bundle as the sweep gas. In Example A, the sweep gas was introduced at a rate of 0.05 L/min. In Example B, the sweep gas was introduced at a rate of 0.1 L/ min. In Example C, the sweep gas was introduced at a rate of 0.2 L/min. The resulting gas phase (containing air and NO) for each example at various currents was analyzed for NO content using chemiluminescence. The results are shown in Table 1.

TABLE 1

| | EXAMPLE A | | | EXAMPLE B | | | EXAMPLE C | |
|---|---|---|---|---|---|---|---|---|
| Air Sweep Gas Rate (L/min) | 0.05 | 0.05 | 0.05 | 0.1 | 0.1 | 0.1 | 0.2 | 0.2 |
| Current (mA) | 5 | 10 | 20 | 5 | 10 | 30 | 5 | 10 |
| NO (ppm) | 317 | 430 | >500 | 196 | 262 | 406 | 103 | 168 |

For each of Examples A, B, and C, higher levels of NO were generated when the current was increased. The results also indicate that the resulting gas phase has a higher concentration of NO when a lower air sweep gas flow rate is utilized.

Figure 11:
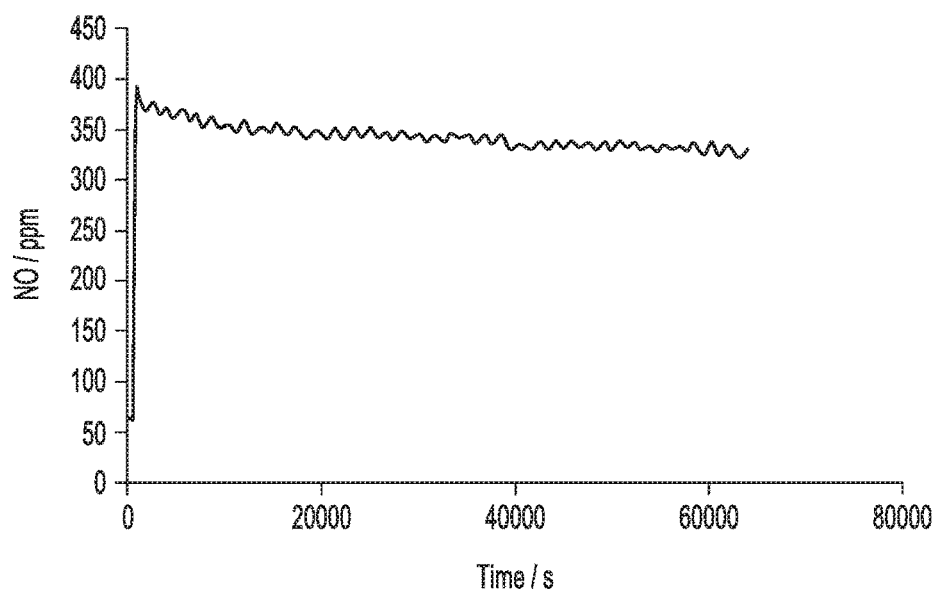
FIG. 11 is a graph depicting the modulation of nitric oxide generation, in terms of the NO ppm level versus time (in seconds), in an output gas stream including NO swept from solution by an air sweep gas at a constant flow rate of 0.05 L/min, where the NO was generated from a bulk aqueous solution of 7 mM CuMe$_3$TACN, 1 M sodium nitrite, and 0.5 M HEPES buffer (pH 7.3), using a constant current method on a 4.5 cm×8.5 cm gold mesh electrode.

The solution and electrochemical cell of this example was also tested over a period of 20 hours at a constant current of 6 mA and an air sweep gas rate of 0.05 L/min. The solution was circulated between the NO generating system and the fiber bundle continuously over the 20 hour time period. These results are shown in FIG. 11. As illustrated, in FIG. 11, a relatively constant level of NO was generated and extracted over the entire time period tested.

Overall, Example 6 illustrates that the fluid recirculation system disclosed herein can utilize an oxygen-containing gas as a sweep gas to pick up electrochemically generated NO and to generate an output gas stream. This example also illustrates that the NO generating system can reuse the solution to continuously generate desirable levels of NO, even if oxygen is introduced into the recirculated solution. Since there is no direct air purging into the solution, any $O_2$ in the solution should be dissolved $O_2$ from the air sweep gas (i.e., about 10 ppm at 100% saturation). This level will not reduce the NO production significantly.

Example 7

An aqueous solution was prepared with 7 mM Cu(II) Me$_3$TACN, 1 M sodium nitrite and 0.5 M HEPES buffer (the solution was buffered to pH 7.3). The working electrode was a 4.5×4.5 cm$^2$ stainless steel mesh, and the reference/counter electrode was a 4.5×4.5 cm$^2$ stainless steel mesh. The generation of NO and the modulation of NO generation were performed by continuously adjusting the voltage to apply constant currents of 0 mA, 5 mA, 10 mA, and 20 mA for different time periods.

Figure 12:
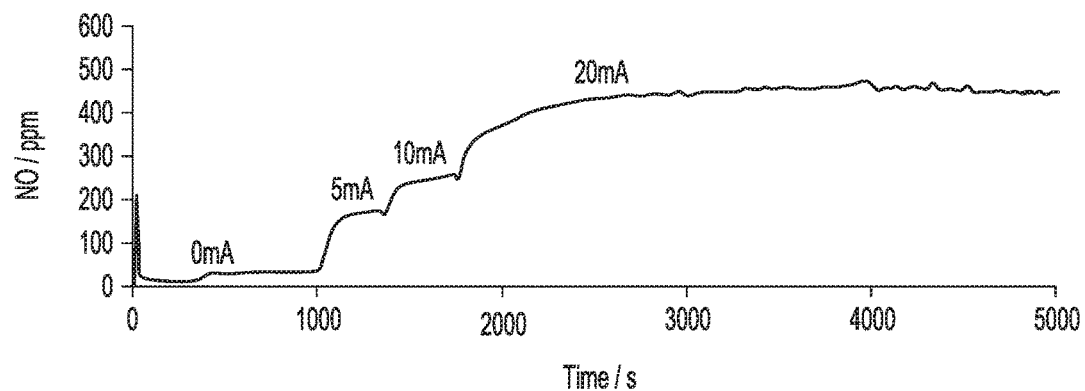
FIG. 12 is a graph depicting the modulation of nitric oxide generation, in terms of the NO ppm level versus time (in seconds), in an output gas stream including NO swept from solution by an oxygen sweep gas at a constant flow rate of 0.05 L/min, where the NO was generated from a bulk aqueous solution of 7 mM CuMe$_3$TACN, 1 M sodium nitrite, and 0.5 M HEPES buffer (pH 7.3), using a constant current method on a 4.5×4.5 cm$^2$ stainless steel electrode.

The solution containing the generated NO was pumped into a fiber bundle, where NO diffused through the fibers and excess solution was recirculated back into the container used for NO generation. Air was introduced into the fiber bundle as the sweep gas at a rate of 0.05 L/min. The resulting gas phase (containing air and NO) for each example at various currents was analyzed for NO content using chemiluminescence. The results are shown in FIG. 12. As depicted in FIG. 12, higher levels of NO were generated when the current was increased.

Figure 13:
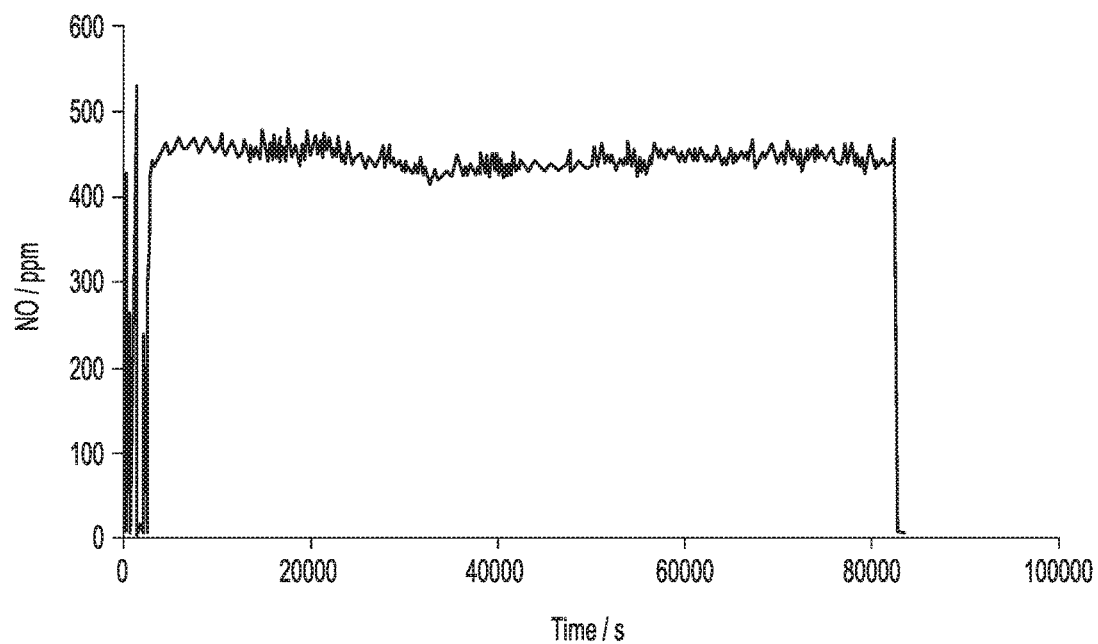
FIG. 13 is a graph depicting the modulation of nitric oxide generation, in terms of the NO ppm level versus time (in seconds), in an output gas stream including NO swept from solution by an oxygen sweep gas at a constant flow rate of 0.05 L/min, where the NO was generated from a bulk aqueous solution of 7 mM $CuMe_3TACN$, 1 M sodium nitrite, and 0.5 M HEPES buffer (pH 7.3), using a constant current method on a 4.5×4.5 $cm^2$ stainless steel electrode.

The solution and electrochemical cell of this example was also tested over a period of 24 hours at a constant current of 20 mA and an air sweep gas rate of 0.05 L/min. The solution was circulated between the NO generating system and the fiber bundle continuously over the 24 hour time period. These results are shown in FIG. 13. As illustrated, in FIG. 13, a relatively constant level of NO was generated and extracted over the entire time period tested.

Overall, Example 7 illustrates that the fluid recirculation system disclosed herein can utilize an oxygen-containing gas as a sweep gas to pick up NO generated by a stainless steel working electrode(s).

It is to be understood that the ranges provided herein include the stated range and any value or sub-range within the stated range. For example, a range from about 100 ppbv to about 100 ppmv should be interpreted to include not only the explicitly recited limits of about 100 ppbv to about 100 ppmv, but also to include individual values, such as 150 ppbv, 50.5 ppmv, 75 ppmv, etc., and sub-ranges, such as from about 300 ppbv to about 30 ppmv, etc.

Furthermore, when "about" is utilized to describe a value, this is meant to encompass minor variations (up to +/− 10%) from the stated value. When applied potential values are discussed, it is to be understood that wider ranges may be suitable. In some of the examples disclosed herein, increasing the magnitude of the cathodic potential pulse (i.e., a more negative cathodic potential) increases the amount of Cu(I)-ligand complex that is generated, and thus also increases the amount of NO generated. As such, it is believed that a broad range is applicable for the applied potential values, the limits of which may depend on the desired amount of Cu(I) species and NO to be generated.

Furthermore, reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

While several examples have been described in detail, it is to be understood that the disclosed examples may be modified. Therefore, the foregoing description is to be considered non-limiting.

What is claimed is:

1. A gas delivery device, comprising:
a nitric oxide generating system, including:
a medium including a source of nitrite ions;
a working electrode in contact with the medium;
a Cu(II)-ligand complex in contact with the working electrode; and
one of: a reference/counter electrode or a reference electrode and a counter electrode in contact with the medium and separated from the working electrode;
an inlet conduit to deliver nitrogen gas to the medium;
an outlet conduit to transport a stream of nitrogen gas and nitric oxide from the medium; and
an inspiratory gas conduit operatively connected to the outlet conduit to introduce an oxygen-containing gas and form an output gas stream of the gas delivery device.

2. The gas delivery device as defined in claim 1, further comprising:
a separator operatively positioned between the outlet conduit and the inspiratory gas conduit, the separator including:
a housing containing a nitric oxide permeable material separating two spaces;
a first housing inlet operatively connected to the outlet conduit to receive, in a first of the two spaces, the stream of nitrogen gas and nitric oxide from the outlet conduit;
a second housing inlet operatively connected to the inspiratory gas conduit to receive, in a second of the two spaces, the oxygen-containing gas, which mixes with nitric oxide diffusing through the nitric oxide permeable material to form the output gas stream; and
a housing outlet conduit to transport the output gas stream to a recipient.

3. The gas delivery device as defined in claim 2 wherein the nitric oxide permeable material is selected from the group consisting of a membrane and a hollow fiber bundle.

4. The gas delivery device as defined in claim 2, further comprising an inhalation unit operatively connected to the housing outlet conduit.

5. The gas delivery device as defined in claim 2, further comprising an oxygenator operatively connected to the housing outlet conduit.

6. The gas delivery device as defined in claim 1, further comprising:
a delivery conduit operatively connected to the outlet conduit and the inspiratory gas conduit; and
an inhalation unit operatively connected to the delivery conduit.

7. The gas delivery device as defined in claim 1, further comprising a sensor in contact with the output gas stream to monitor a nitric oxide level of the output gas stream.

8. The gas delivery device as defined in claim 1 wherein:
the Cu(II)-ligand complex is selected from the group consisting of Cu(II)-tri(2-pyridylmethyl)amine, Cu(II)-tri(2-dimethylamino)ethyl]amine, Cu(II)-tri(2-pyridylmethyl)phosphine, Cu(II)-1,4,7-trimethyl-1,4-7-triazacyclononane, Cu(II)-1,4,7-triethyl-1,4,7-triazacyclononane, Cu(II)-1,4,7-tripropyl-1,4,7-triazacyclononane, Cu(II)-1,4,7-triisopropyl-1,4,7-triazacyclononane, Cu(II)-(N,N-bis-(2-pyridylmethyl)amine-N-ethylate), Cu(II)-(N,N-bis-(2-pyridylmethyl)amine-N-propanoate), Cu(II)-(N,N-bis-(2-pyridylmethyl)amine-N-butylate), Cu(II)-(N,N-bis-(2-pyridylethyl)amine-N-ethylate), Cu(II)-(N,N-bis-(2-pyridylethyl)amine-N-propanoate), Cu(II)-(N,N-bis-(2-pyridylethyl)amine-N-butylate, Cu(II)-(N,N-bis-(2-pyridylmethyl)amine-N-methyl-phenolate), Cu(II)-(N,N-bis-(2-pyridylmethyl)amine-N-ethyl-phenolate), Cu(II)-(N,N-bis-(2-pyridylmethyl)amine-N-propyl-phenolate), Cu(II)-(N,N-bis-(2-pyridylethyl)amine-N-methyl-phenolate), Cu(II)-(N,N-bis-(2-pyridylethyl)amine-N-ethyl-phenolate), Cu(II)-(N,N-bis-(2-pyridylethyl)amine-N-propyl-phenolate), Cu(II)-3-((2-(pyridin-2-yl)ethyl)(pyridin-2-ylmethyl)amino) ethylate , Cu(II)-3-((2-(pyridin-2-yl)ethyl)(pyridin-2-ylmethyl)amino)propanoate, Cu(II)-3-((2-(pyridin-2-yl)ethyl)(pyridin-2-ylmethyl)amino)butylate, Cu(II)-2-(pyridin-2-yl)-N,N-bis(pyridin-2-ylmethyl)ethan-1-amine, Cu(II)-2,2'-(2-(2-(pyridin-2-yl)ethyl)butane-1,4-diyl)dipyridine, and combinations thereof; and the source of nitrite ions is any water soluble, inorganic or organic nitrite salt.

9. The gas delivery device as defined in claim 1 wherein the working electrode is selected from the group consisting of platinum, gold, carbon, a carbon coated material, mercury, stainless steel, a base electron conducting material having a thin film of platinum thereon, and a base electron conducting material having a thin film of gold thereon.

10. The gas delivery device as defined in claim 1, further comprising:
an oxygen scrubber operatively connected to the inlet conduit; and
a pump operatively connected to the oxygen scrubber, the pump to introduce ambient air into the oxygen scrubber.

11. The gas delivery device as defined in claim 10 wherein the oxygen scrubber includes a solution or a particle bed to at least partially remove oxygen from the ambient air to generate a nitrogen purge gas stream including the nitrogen gas.

12. The gas delivery device as defined in claim 1 wherein the Cu(II)-ligand complex is dissolved or dispersed in the medium.

13. The gas delivery device as defined in claim 1 wherein the Cu(II)-ligand complex is immobilized on a surface of the working electrode.

14. A gas delivery device, comprising:
a nitric oxide generating system, including:
a first housing;
a medium contained in the first housing, the medium including a source of nitrite ions;
a working electrode in contact with the medium;
a Cu(II)-ligand complex in contact with the working electrode; and
one of: a reference/counter electrode or a reference electrode and a counter electrode in contact with the medium and separated from the working electrode;
a nitric oxide extraction device, including:
a second housing;
a nitric oxide permeable medium positioned in the second housing;
a space at least partially surrounding the nitric oxide permeable medium, the space including an input area to receive a nitric-oxide containing solution from the nitric oxide generating system and an output area to transport an at least substantially reduced nitric-oxide solution out of the nitric oxide extraction device;
an inlet conduit to deliver a sweep gas to the nitric oxide permeable medium, the sweep gas being selected from the group consisting of nitrogen gas, an oxygen-containing gas, and combinations thereof; and
an outlet conduit to transport a mixed gas stream from the nitric oxide permeable medium, the mixed gas stream including the nitric oxide and the sweep gas; and
a fluid recirculation system fluidly connecting the first housing and the second housing.

15. The gas delivery device as defined in claim 14 wherein the sweep gas is the nitrogen gas, and wherein the gas delivery device further comprises an inspiratory gas conduit operatively connected with the outlet conduit to introduce an oxygen-containing gas to the mixed gas stream to form an output gas stream.

16. The gas delivery device as defined in claim 15, further comprising:
a delivery conduit operatively connected to the outlet conduit and the inspiratory gas conduit; and
an inhalation unit operatively connected to the delivery conduit.

17. The gas delivery device as defined in claim 14 wherein the fluid recirculation system includes:
a first conduit connecting an outlet of the first housing to an inlet of the second housing;
a second conduit connecting an outlet of the second housing to an inlet of the first housing; and
a pump to transport the nitric-oxide containing solution through the first conduit into the nitric oxide extraction device and to transport the at least substantially reduced nitric-oxide solution through the second conduit into the nitric oxide generating system.

18. The gas delivery device as defined in claim 14, further comprising an oxygenator operatively connected to the outlet conduit.

19. The gas delivery device as defined in claim 15, further comprising a sensor in contact with the output gas stream to monitor a nitric oxide level of the output gas stream.

20. The gas delivery device as defined in claim 14 wherein:
the Cu(II)-ligand complex is selected from the group consisting of Cu(II)-tri(2-pyridylmethyl)amine, Cu(II)-tri(2-dimethylamino)ethyl]amine, Cu(II)-tri(2-pyridylmethyl)phosphine, Cu(II)-1,4,7-trimethyl-1,4-7-triazacyclononane, Cu(II)-1,4,7-triethyl-1,4-7-triazacyclononane, Cu(II)-1,4,7-tripropyl-1,4-7-triazacyclononane, Cu(II)-1,4,7-triisopropyl-1,4-7-triazacyclononane, Cu(II)-(N,N-bis-(2-pyridylmethyl)amine-N-ethylate), Cu(II)-(N,N-bis-(2-pyridylmethyl)amine-N-propanoate), Cu(II)-(N,N-bis-(2-pyridylmethyl)amine-N-butylate), Cu(II)-(N,N-bis-(2-pyridylethyl)amine-N-ethylate), Cu(II)-(N,N-bis-(2-pyridylethyl)amine-N-propanoate), Cu(II)-(N,N-bis-(2-pyridylethyl)amine-N-butylate, Cu(II)-(N,N-bis-(2-pyridylmethyl)amine-N-methyl-phenolate), Cu(II)-(N,N-bis-(2-pyridylmethyl)amine-N-ethyl-phenolate), Cu(II)-(N,N-bis-(2-pyridylmethyl)amine-N-propyl-phenolate), Cu(II)-(N,N-bis-(2-pyridylethyl)amine-N-methyl-phenolate), Cu(II)-(N,N-bis-(2-pyridylethyl)amine-N-ethyl-phenolate), Cu(II)-(N,N-bis-(2- pyridylethyl)amine-N-propyl-phenolate), Cu(II)-3-((2-(pyridin-2-yl)ethyl)(pyridin-2-ylmethyl)amino) ethylate , Cu(II)-3-((2-(pyridin-2-yl)ethyl)(pyridin-2-ylmethyl)amino)propanoate, Cu(II)-3-((2-(pyridin-2-yl)ethyl)(pyridin-2-ylmethyl)amino)butylate, Cu(II)-2-(pyridin-2-yl)-N,N-bis(pyridin-2-ylmethyl)ethan-1-amine, Cu(II)-2,2'-(2-(2-(pyridin-2-yl)ethyl)butane-1,4-diyl)dipyridine, and combinations thereof; and
the source of nitrite ions is any water soluble, inorganic or organic nitrite salt.

21. The gas delivery device as defined in claim 14 wherein the working electrode is selected from the group consisting of platinum, gold, carbon, a carbon coated material, mercury, a base electron conducting material having a thin film of platinum thereon, and a base electron conducting material having a thin film of gold thereon.

22. The gas delivery device as defined in claim 14 wherein the sweep gas is the nitrogen gas, and wherein the gas delivery device further comprises:
    an oxygen scrubber operatively connected to the inlet conduit; and
    a pump operatively connected to the oxygen scrubber, the pump to introduce ambient air into the oxygen scrubber.

23. The gas delivery device as defined in claim 22 wherein the oxygen scrubber includes a solution or a particle bed to at least partially remove oxygen from the ambient air to generate a nitrogen purge gas including the nitrogen gas.

24. The gas delivery device as defined in claim 14 wherein the Cu(II)-ligand complex is dissolved or dispersed in the medium.

25. The gas delivery device as defined in claim 14 wherein the Cu(II)-ligand complex is immobilized on a surface of the working electrode.

26. A method, comprising:
    applying a cathodic voltage or current to a working electrode positioned in contact with a Cu(II)-ligand complex and with a medium including a source of nitrite ions, thereby reducing the Cu(II)-ligand complex to a Cu(I)-ligand complex which reacts with nitrite from the source of nitrite ions to generate nitric oxide (NO);
    sweeping the nitric oxide using nitrogen gas to form a stream of nitrogen gas and nitric oxide; and
    introducing an oxygen-containing gas to mix with the stream of nitrogen gas and nitric oxide to form an output gas stream.

27. The method as defined in claim 26, further comprising modulating a flux of the generated nitric oxide by any of altering an amount of a surface area of the working electrode that is exposed to the medium, or altering a concentration of the Cu(II)-ligand complex, or altering a concentration of the source of nitrite ions in the medium, or altering a magnitude of the applied cathodic voltage over time, or altering a magnitude the applied cathodic current over time.

28. The method as defined in claim 26, further comprising:
    monitoring a nitric oxide level of the output gas stream; and
    based on the nitric oxide level of the output gas stream, one of:
        maintaining the applied cathodic voltage or current; or
        adjusting the applied cathodic voltage or current to increase NO production when the nitric oxide level of the output gas stream is below a target level; or
        adjusting the applied cathodic voltage or current to decrease NO production when the nitric oxide level of the output gas stream is above the target level.

29. The method as defined in claim 26 wherein the applying of the cathodic voltage or current includes:
    applying the cathodic voltage;
    monitoring a current at the working electrode during the application of the cathodic voltage; and
    selectively adjusting the cathodic voltage to maintain an at least substantially constant current at the working electrode.

* * * * *